(12) United States Patent
Peeters

(10) Patent No.: US 10,448,843 B1
(45) Date of Patent: Oct. 22, 2019

(54) FLOW DETECTION

(71) Applicant: Verily Life Sciences LLC, Mountain View, CA (US)

(72) Inventor: Eric Peeters, San Jose, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 682 days.

(21) Appl. No.: 14/332,745

(22) Filed: Jul. 16, 2014

(51) Int. Cl.
*A61B 5/0205* (2006.01)
*A61B 5/00* (2006.01)
*A61B 18/04* (2006.01)

(52) U.S. Cl.
CPC ........ *A61B 5/02055* (2013.01); *A61B 5/0059* (2013.01); *A61B 5/681* (2013.01); *A61B 18/04* (2013.01)

(58) Field of Classification Search
None
See application file for complete search history.

(56) References Cited

U.S. PATENT DOCUMENTS

| | | | | |
|---|---|---|---|---|
| 4,228,805 A | * | 10/1980 | Rosen | A61B 5/026 600/504 |
| 5,738,683 A | * | 4/1998 | Osypka | A61B 5/0422 606/39 |
| 5,769,791 A | * | 6/1998 | Benaron | A61B 5/0086 600/473 |
| 5,954,659 A | | 9/1999 | Curley et al. | |
| 5,967,986 A | * | 10/1999 | Cimochowski | A61B 5/0031 600/454 |
| 6,514,278 B1 | * | 2/2003 | Hibst | A61B 18/203 606/11 |
| 2003/0120162 A1 | * | 6/2003 | Bowman | A61B 5/028 600/505 |
| 2004/0171956 A1 | * | 9/2004 | Babashan | A61B 5/02438 600/509 |
| 2005/0182342 A1 | * | 8/2005 | Dinsmoor | A61B 5/073 600/593 |
| 2005/0204811 A1 | * | 9/2005 | Neff | A61B 5/00 73/204.11 |
| 2007/0106139 A1 | | 5/2007 | Nagata et al. | |
| 2007/0118045 A1 | * | 5/2007 | Naghavi | A61B 5/01 600/549 |

(Continued)

*Primary Examiner* — Etsub D Berhanu
*Assistant Examiner* — Jairo H Portillo
(74) *Attorney, Agent, or Firm* — McDonnell Boehnen Hulbert & Berghoff LLP

(57) ABSTRACT

Methods and systems are provided for measuring the flow of fluid (e.g., blood) in vasculature of a human by heating the fluid in a portion of the vasculature and detecting the temperature of fluid in and/or tissue proximate to a downstream portion of the vasculature. The blood is heated by emitting energy through an external body surface into the portion of vasculature. The temperature of the downstream portion of vasculature is detected by an infrared sensor receiving infrared light from the body and/or a temperature sensor in thermally conductive contact with the body. The flow of fluid in the portion of vasculature can be determined by determining a latency between a change in the detected temperature relative to a change in the emitted energy, by determining a difference between the detected temperature and a detected temperature of another portion of the body, or by some other method.

18 Claims, 10 Drawing Sheets

(56) References Cited

U.S. PATENT DOCUMENTS

| | | | |
|---|---|---|---|
| 2007/0177017 A1* | 8/2007 | Kyle | A61B 5/01 |
| | | | 348/207.99 |
| 2009/0234404 A1* | 9/2009 | Fitzgerald | A61N 1/36514 |
| | | | 607/9 |
| 2010/0168676 A1* | 7/2010 | Datta | A61B 18/1492 |
| | | | 604/171 |
| 2010/0179439 A1* | 7/2010 | Kuschel | A61B 5/022 |
| | | | 600/485 |
| 2012/0248985 A1 | 10/2012 | Lin et al. | |
| 2013/0095459 A1* | 4/2013 | Tran | A61B 5/6816 |
| | | | 434/247 |

* cited by examiner

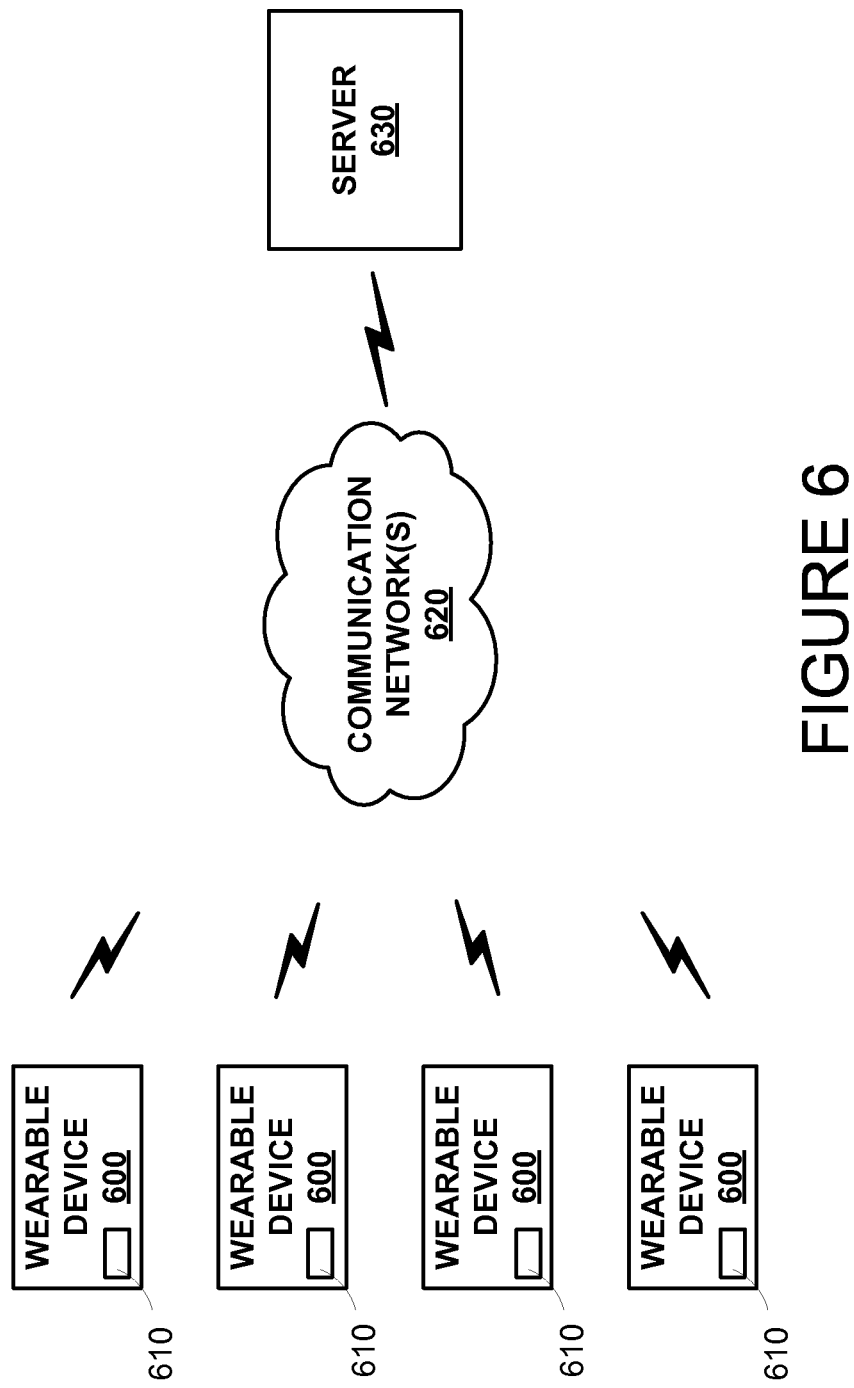

FLOW DETECTION

BACKGROUND

Unless otherwise indicated herein, the materials described in this section are not prior art to the claims in this application and are not admitted to be prior art by inclusion in this section.

The flow rate of blood in a blood vessel of a person can be related to a variety of properties of the state of health of the person. For example, the flow rate of blood in a vessel can be related to a heart rate, a blood pressure, a blood flow and/or a pressure profile. The flow rate of blood in one or more blood vessels of the person could be detected in a clinical environment to determine a health state or other medical information about the person. Detection of the flow rate of blood in a blood vessel of a person over a protracted period of time (e.g., for a period of hours or days) in a variety of environments (e.g., a home environment, a work environment) could allow the determination of information about a health state of the person. Such information could be used to diagnose an adverse health state (e.g., heart disease, aortic stenosis, aortic regurgitation) of the person, to develop a baseline 'healthy' data set for the person, to detect the early stages of the development of an adverse health condition, to inform an exercise regimen of the person, and/or to enable some other application.

SUMMARY

Some embodiments of the present disclosure provide a device including: (i) an energy source, wherein the energy source is configured to emit energy through an external body surface at a first location into a portion of subsurface vasculature such that fluid in the portion of subsurface vasculature is heated; (ii) a downstream temperature sensor, wherein the downstream temperature sensor is configured to measure a temperature of a downstream region of tissue via the external body surface at a second location, wherein the downstream region of tissue is downstream from the first location with respect to fluid flow in the portion of subsurface vasculature; and (iii) a controller, wherein the controller is configured to (a) operate the energy source and the downstream temperature sensor and (b) determine a flow rate of fluid in the portion of subsurface vasculature based at least on the temperature measured by the downstream temperature sensor.

Some embodiments of the present disclosure provide a method including: (i) heating fluid in a portion of subsurface vasculature, wherein heating fluid in the portion of subsurface vasculature comprises emitting energy through an external body surface at a first location into the portion of subsurface vasculature using an energy source; (ii) measuring a temperature of a downstream region of tissue via the external body surface at a second location using a downstream temperature sensor, wherein the downstream region of tissue is downstream from the first location with respect to fluid flow in the portion of subsurface vasculature; and (iii) determining a flow rate of fluid in the portion of subsurface vasculature based at least on the temperature measured by the downstream temperature sensor.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 6 is a block diagram of an example system that includes a plurality of wearable devices in communication with a server.

DETAILED DESCRIPTION

Figure 1A:
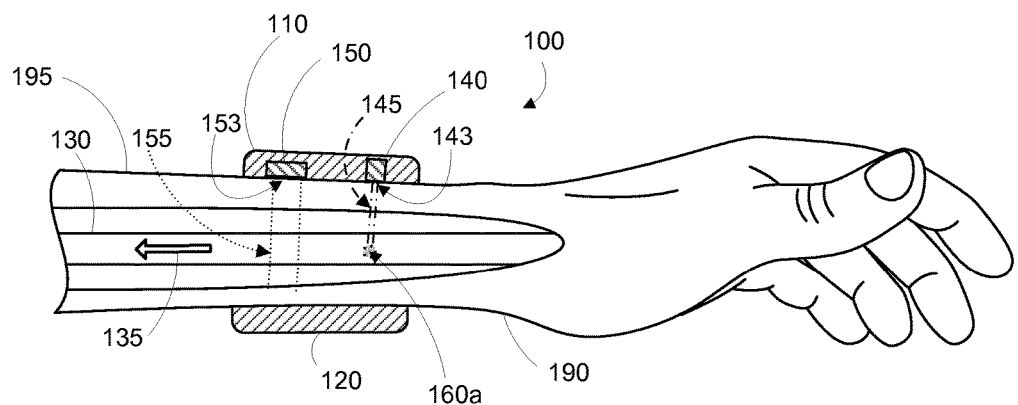
FIG. 1A is side partial cross-sectional view of an example system, while measuring blood flow in a human wrist.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where non-invasive detection of a flow property is desired. The environment may be any living or non-living body or a portion thereof, a gel, an emulsion, a fluid conduit, a fluid reservoir, etc. For example, one of skill in the art will recognize that the embodiments disclosed herein may be used to sense properties of fluid flow in a water treatment system. Moreover, while the present disclosure describes embodiments for use in vivo, one of skill in the art will also recognize that in vitro applications are possible as well. Accordingly, the environment may also include a test tube or other vessel for holding a fluid.

I. Overview

The flow rate of fluid (e.g., blood) in a portion of subsurface vasculature of a person could be detected by heating the fluid using energy emitted by an energy source (e.g., a laser, a light-emitting diode, an ultrasonic emitter, a resistive heater or other contact heat source) such that the fluid experiences an increase in temperature (i.e., is heated). A temperature sensor could be disposed at a specified location relative to the energy source and configured to detect a temperature of a region of tissue downstream from the portion of subsurface vasculature containing fluid heated by the energy source. An amplitude, a change in amplitude, a waveform, a rise time, a relative timing, a latency, or some other property of the detected temperature could be used to determine the flow rate of the fluid in the portion of vasculature. For example, the temperature sensor could be configured to detect the temperature of a region of tissue that is downstream from the portion of subsurface vasculature heated by the energy source; a difference in time between a change in the intensity of the emitted energy and a change (e.g., a rise) in the detected temperature of the downstream region could be determined and used to determine the flow rate of the fluid (e.g., by dividing a distance between the downstream region and the portion of subsurface vasculature heated by the energy source by the determined difference in time). Other configurations and operations of an energy source and temperature sensor to determine and/or detect a flow rate of fluid in a portion of vasculature are anticipated.

An energy source could be configured and/or operated to emit energy to heat fluid in a portion of subsurface vasculature in a variety of ways according to a variety of applications. The emitted energy could include light energy (e.g., a beam of visible, infrared, ultraviolet, or some other type of illumination), thermal energy (e.g., heat generated by a resistive heater or some other type of heater and conducted, radiated, or otherwise transferred to the fluid), acoustic energy (e.g., ultrasonic waves configured to heat the fluid), and/or some other energy. The emitted energy could have a specified amplitude, intensity, wavelength, or some other specified property. The energy source could be operated to continuously emit energy, to generate pulses of energy, to change a property (e.g., intensity) of an emitted energy from one period of time to another, and/or to generate an emitted energy having some other property or properties dependent on time in some other way. In some examples, the emitted energy could have a first intensity during a first period of time and a second intensity during a second period of time, and a property of a detected temperature (e.g., a level of temperature, a relative timing of a temperature change, a waveform of the temperature over time) related to the first and second intensities and/or the timing of the first and second periods of time could be used to determine a flow rate of the fluid in the portion of subsurface vasculature. The energy source could be operated relative to a temperature detected using the temperature sensor; for example, the energy source could be operated to emit energy having a specified intensity such that a detected temperature and/or detected change in temperature is substantially equal to a specified value.

Multiple temperature sensors could be included to detect the temperature of multiple regions of tissue proximate to the portion of subsurface vasculature heated by the energy source and to allow for determination of a flow rate of fluid in the portion of subsurface vasculature and/or other information. For example, a first temperature sensor could be configured to detect a temperature of a region tissue downstream from the portion of subsurface vasculature (e.g., a downstream portion of subsurface vasculature) heated by the energy source and a second temperature sensor could be configured to detect a temperature of a region of tissue that is not downstream from the portion of subsurface vasculature heated by the energy source (e.g., an upstream portion of subsurface vasculature). A difference between the temperatures detected by the first and second temperature sensors could be used to determine a flow rate of fluid in the portion of subsurface vasculature. For example, the temperatures measured by the first and second temperature sensors could include a first, common-mode signal (e.g., a baseline body temperature of the regions of tissue surrounding the portion of subsurface vasculature), and the temperature measured by the first (i.e., downstream) temperature sensor could further include a second signal related to the heating of the fluid by the energy source. The difference between the temperatures measured by the first and second temperature sensors can provide a signal related to the heating of the fluid by the energy source that has a higher signal to noise ratio than would otherwise be achieved by measuring the temperature at only a single point. Additionally or alternatively, a change in the temperature detected by the second sensor related to a change in the emitted energy could be used to determine a thermal conductivity or other property of tissue proximate to the subsurface vasculature. The determined thermal conductivity or other property could be used, in combination with a change in or other property of the temperature detected using the first temperature sensor, to determine a flow rate of fluid in the subsurface vasculature. The temperature sensor could include an infrared camera and/or an array of temperature sensors and could be used to image the temperature across one or more regions of tissue proximate to the portion of subsurface vasculature heated by the energy source. Images of the region(s) of tissue could be used to determine a flow rate of fluid in the portion of subsurface vasculature, a thermal conductivity of the tissue, a location, shape, or other properties of the portion of subsurface vasculature, or other information about the body and/or health state of a person.

In some examples, the fluid could be blood. In other example, the fluid could be lymph, cerebrospinal fluid, or some other type of body fluid. Determined flow rates of blood in a portion of subsurface vasculature could be used to determine a blood pressure of the blood in the portion of subsurface vasculature and/or in some other part of a person's body (e.g., an aortic blood pressure). A detected flow rate of blood could be related to a mean blood pressure, a diastolic blood pressure, a systolic blood pressure, an instantaneous blood pressure, or some other information related to blood pressure in the portion of subsurface vasculature or elsewhere. For example, a relationship could be determined between the flow rate of blood in a particular portion of subsurface vasculature and a blood pressure in the particular portion of subsurface vasculature. Such a relationship could be used to determine a systolic blood pressure, diastolic blood pressure, a mean blood pressure, or some other property of blood pressure in the particular portion of subsurface vasculature based on a detected flow rate of blood in the particular portion of subsurface vasculature over time. In some examples, a relationship between the flow rate of blood and the pressure of blood in a portion of subsurface vasculature could be determined by detecting the flow rate of the blood when the portion of subsurface vasculature (and surrounding tissues) is increased and/or decreased in elevation relative to the heart of the body containing the portion of subsurface vasculature (e.g., by raising and/or lowering an arm containing the portion of subsurface vasculature). For example, a difference between a flow rate detected when the portion of subsurface vasculature is at a first elevation and a flow rate detected when the portion of subsurface vasculature is at a second elevation could be related to a difference between the first and second elevations (e.g., to a difference in pressure corresponding to a difference in elevation in a water column that corresponds to the difference between the first and second elevations).

The above described methods may be performed using a wearable device. The term "wearable device," as used in this disclosure, refers to any device that is capable of being worn at, on, or in proximity to a body surface, such as a wrist, ankle, waist, chest, ear, eye or other body part. In order to take in vivo measurements in a non-invasive manner from outside of the body, the wearable device may be positioned on a portion of the body where subsurface vasculature or some other flow environment is easily observable. The device may be placed in close proximity to the skin or tissue, but need not be touching or in intimate contact therewith. A mount, such as a belt, wristband, ankle band, headband, etc. can be provided to mount the device at, on or in proximity to the body surface. The mount may prevent the wearable device from moving relative to the body to reduce measurement error and noise. Further, the mount may be an adhesive substrate for adhering the wearable device to the body of a wearer. The temperature sensor, energy source, and, in some examples, a controller and/or other components, may be provided on the wearable device.

In other embodiments, the above described methods may be performed using a stationary measurement device to which a user is brought into contact or proximity with or as a device that may be temporarily placed or held against a body surface during one or more measurement periods. In other embodiments, the above described system may be implemented to detect flow rates or other properties of fluids in environments that are not a part of a human body, e.g., an in vitro or other sample container, an outdoor environment, an animal body, or some other environment of interest that can be heated in a localized region by an energy-source-emitted energy such that the heating is related to the temperature of a region of the environment that can be detected and that has one or more properties related to the flow rate of fluid in the environment.

It should be understood that the above embodiments, and other embodiments described herein, are provided for explanatory purposes, and are not intended to be limiting.

II. Illustrations of Flow Property Detection

A flow rate of blood in a portion of vasculature can be detected by heating blood in the portion of vasculature and detecting the temperature of tissues (e.g., tissues proximate to another portion of vasculature that is downstream relative to the portion of vasculature wherein the blood is heated) at one or more specified locations relative to the portion of vasculature. The flow rate of blood in the portion of vasculature could be related to a level of temperature, a change in a level of temperature, a time-dependence of temperature, or some other property of temperature of the one or more tissues at the one or more specified locations. The relationship between the flow rate of the blood, the heating of the blood by emitted energy, and the one or more detected temperatures could be related to conduction of heat by tissues and/or blood proximate to the portion of subsurface vasculature, convection of heat due to the flow of blood within the vasculature, and/or other thermodynamic processes.

Figure 1B:
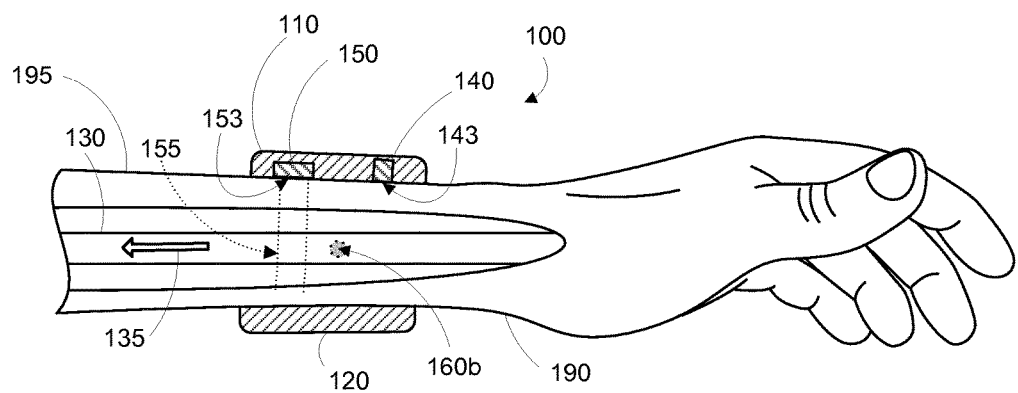
FIG. 1B is side partial cross-sectional view of the example system illustrated in FIG. 1A, while measuring blood flow in a human wrist.
Figure 1C:
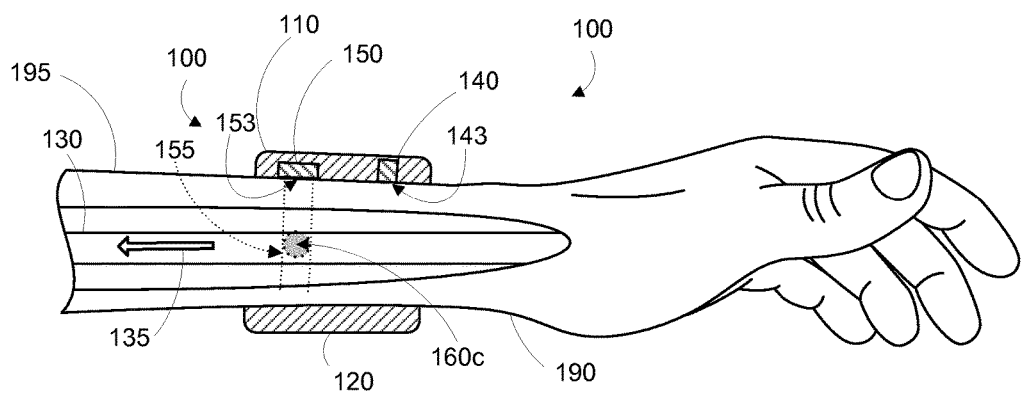
FIG. 1C is side partial cross-sectional view of the example system illustrated in FIG. 1A, while measuring blood flow in a human wrist.

FIGS. 1A-1C are partial cross-sectional side views of a human wrist 105 illustrating the operation of an example wearable device 100. In the example shown in FIGS. 1A-1C, the wearable device 100 includes a measurement platform 110 mounted on a strap or wrist-band 120 and oriented on the posterior side 195 of the wearer's wrist. Measurement platform 110 is positioned over a portion of the wrist where subsurface vasculature 130 is easily heated and/or observed. The wearable device 100 includes energy source 140 configured to emit energy 145 through an external body surface at a first location 143 (e.g., skin of a posterior side 195 of the wearer's wrist at the first location 143) into the portion of subsurface vasculature 130. The wearable device 100 additionally includes a downstream temperature sensor 150 configured to detect the temperature of a downstream region of tissue 155 (including, e.g., a downstream portion of vasculature and other tissues proximate thereto) by receiving infrared light via the external body surface at a second location 153. The wearable device 100 additionally includes a controller (not shown) configured to operate the energy source 140 and the downstream temperature sensor 150 to determine a flow rate of blood in the portion of subsurface vasculature 130. The wearable device 100 could include further elements, e.g., a user interface, a wireless transceiver, a battery or other power source, or some other elements.

To illustrate the operation of the wearable device 100, the movement of an example heated portion of blood (160a, 160b, 160c in FIGS. 1A, 1B, and 1C, respectively) due to blood flow 135 in the portion of subsurface vasculature 130 is illustrated in FIGS. 1A-1C. FIG. 1A illustrates the state of the wearable device 100 and subsurface vasculature 130 during a first period of time when the energy source 140 is being operated to heat the example portion of blood 160a in the portion of subsurface vasculature 130 by emitting the energy 145. FIG. 1B illustrates the state of the wearable device 100 and subsurface vasculature 130 during a second period of time after the first period of time when the example heated portion of blood 160a has been transported downstream (and expanded due to convection, diffusion, conduction, and/or other heat and fluid transport processes) by the blood flow 135 in the portion of subsurface vasculature 130 to become example heated portion of blood 160b. FIG. 1C illustrates the state of the wearable device 100 and subsurface vasculature 130 during a third period of time after the second period of time when the example heated portion of blood 160b has been transported further downstream (and expanded due to convection, diffusion, conduction, and/or other heat and fluid transport processes) by the blood flow 135 in the portion of subsurface vasculature 130 to become example heated portion of blood 160c. During the third period of time, example heated portion of blood 160c is located within the downstream region of tissue 155 such that a temperature measured by the downstream temperature sensor 150 during the third period of time is related to the temperature of the example heated portion of blood 160c. The temperature measured by the downstream temperature sensor 150 during the third period of time is thus further related to any properties or processes of the blood (e.g., a flow rate or other property of the blood flow 135, a blood pressure), the wearable device 100 (e.g., an amplitude, timing, or other properties of the emitted energy 145), the portion of subsurface vasculature 130 (e.g., a diameter, an internal smoothness), or other related systems or tissues having effects on the example heated portion of blood 160c and/or other elements within or proximate to the downstream region of tissue 155.

The example heated portions of blood 160a, 160b, 160c as illustrated in FIGS. 1A-1C, respectively, are intended to illustrate the rough locations and extents of regions of blood in the portion of subsurface vasculature 130 that have a higher temperature due to the operation of the energy source 140 (i.e., the heating of blood in the portion of subsurface vasculature by emitting the energy 145) than if the energy source 140 had not been operated. The movement (e.g., convection, diffusion, mass transfer) of blood in the portion of subsurface vasculature (due to the blood flow 135, deformation of the portion of subsurface vasculature 130, activation of muscles in the arm, turbulence, or other hydrodynamic processes), the conduction and/or radiation of heat by the blood and/or neighboring tissues, and other mass and heat transfer processes can cause changes in the location, temperature, extent, shape, or other properties of a heated region of blood in a subsurface portion of vasculature. Generally, a heated region of blood will be translated slightly preferentially in the direction of blood flow and will expand and experience a reduction in temperature (due, e.g., to heat conduction, convection, and diffusion).

As a result, tissues proximate to the blood (e.g., walls of downstream portions of vasculature, other tissues proximate thereto) could also experience heating and/or a change in temperature related to the operation of the energy source (i.e., the heating of blood in the portion of subsurface vasculature) and the blood flow 135 (e.g., a flow rate of the blood), among other things. The temperature sensor 150 is illustrated in FIGS. 1A-1C as an infrared light detector configured to receive infrared light from the downstream region of tissue 155 having an intensity or other property (e.g., wavelength, spectral profile) that is related to the temperature of the blood within the portion of subsurface vasculature (e.g., example heated portion of blood 160c) or some other tissue or tissues within or proximate to the downstream region of tissue 155. However, the temperature sensor 150 could be configured differently. In some examples, the shape and/or size of the downstream region of tissue 155 whose temperature is measured by the temperature sensor 150 could be different. For example, the temperature sensor 150 could include optics or be otherwise configured such that the downstream region of tissue 155 whose temperature is measured by the temperature sensor 150 was a small region centered on and/or substantially contained within the portion of vasculature. In some examples, the temperature sensor 150 could include a temperature-sensitive element (e.g., a thermistor, a thermocouple, a silicon bandgap thermometer) in thermal contact with the external body surface at a second location 153 such that the temperature sensor 150 could measure the temperature of a downstream region of tissue proximate to the second location 153 whose temperature, via conduction, radiation, convection, or other processes, is related to the temperature of blood in the portion of subsurface vasculature 130 and thus could be used to determine the flow rate of blood in the portion of subsurface vasculature 130.

Figure 2A:
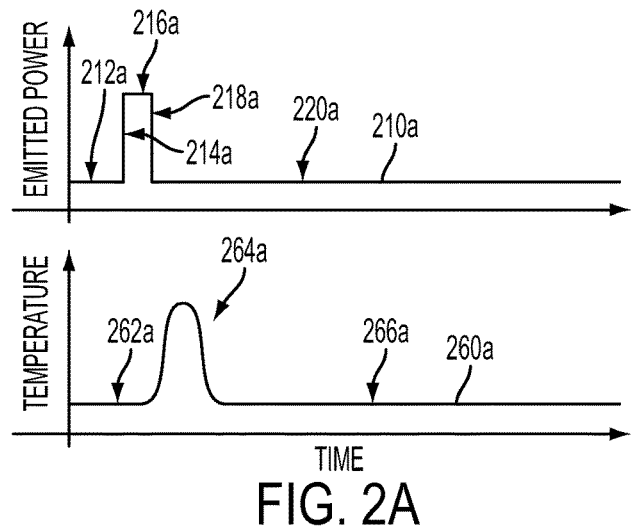
FIG. 2A illustrate example emitted energy and output waveforms that could be generated by an example flow detection system.

The heating of blood in the portion of subsurface vasculature 130 by the energy source 140 during the first period of time and the movement of the resulting example heated portion of blood 160a-c through the portion of subsurface vasculature 130 in the first, second, and third periods of time (as illustrated in FIGS. 1A-C, respectively) results in the downstream region of tissue 155 experiencing a change in temperature. FIG. 2A illustrates an example emitted energy 210a and an example downstream region of tissue temperature waveform 260a corresponding to the scenario described in relation to FIG. 1A-1C. That is, emitted energy waveform 210a includes a pulse of energy 216a (corresponding to the heating of the example portion of blood 160a by the emitted energy 145 emitted by the energy source 140 during the first period of time) having a specified pulse amplitude, specified pulse width, or other properties related to the operation of the energy source 140.

The first period of time of FIG. 1A includes the period of time between the rising edge 214a and the falling edge 218a of the pulse of energy 216a. The emitted energy waveform 210a has a specified lower amplitude (e.g., a zero amplitude corresponding to no energy emitted by the energy source 140) before 212a and after 220a the pulse. The period after 220a the pulse includes the second and third periods of time of FIGS. 1B and 1C. The corresponding downstream temperature waveform 260a includes a pulse of increased temperature 264a. The third period of time of FIG. 1C is temporally proximate to the timing of the pulse of increased temperature 264a. Before 262a and after 266a the pulse of increased temperature 264a, the downstream region of tissue has a baseline temperature related to the environment of the downstream region of tissue 155 (e.g., an ambient temperature, metabolism of cells in or proximate to the downstream region of tissue 155, a core body temperature, a mean flow rate of blood in the portion of subsurface vasculature 130).

Properties of the pulse of increased temperature 264a could be related to a flow rate of blood in the portion of subsurface vasculature 130 and could thus be detected and/or measured in order to determine the flow rate of blood in the portion of subsurface vasculature 130. A relative timing (i.e., a time difference) between a feature of the pulse of increased temperature 264a and a feature of the pulse of energy 216a could be related to the flow rate of blood. For example, a latency or time difference between the peak of the pulse of increased temperature 264a and the rising edge 214a of the pulse of energy 216a could be related to the flow rate of blood, e.g., the flow rate could be related to a specified distance between the energy source 140 and the downstream region of tissue 155 divided by such a time difference. A duration of the pulse of increased temperature 264a could be related to a flow rate of blood in the portion of subsurface vasculature 130 (e.g., a wider pulse of increased temperature 264a could correspond to a slower flow rate of blood). A value of temperature during the pulse of increased temperature 264a (e.g., a peak temperature, a ratio of a peak temperature over a baseline temperature) could be related to a flow rate of blood in the portion of subsurface vasculature 130 (e.g., a higher flow rate of blood could correspond to a lower peak temperature). Additional properties, features, and/or combinations thereof of a pulse of increased temperature (e.g., 264a) of a region of tissue downstream relative to a portion of subsurface vasculature containing blood heated by a pulse of energy (e.g., 216a) could be related to the flow rate of blood in the portion of subsurface vasculature.

The energy source 140 could be operated to heat blood in the portion of subsurface vasculature 130 by emitting energy according to some other pattern or patterns of activation than the example pulse of energy 216a illustrated in FIG. 2A. For example, the energy source 140 could be operated to emit a plurality of pulses of energy, to emit energy having a sinusoidally-varying amplitude, to emit trapezoidal or otherwise shaped pulses of energy, to emit energy having a specified amplitude for a protracted period of time, or according to some other-time-dependent pattern of amplitude or some other property of the energy (e.g., a wavelength, a polarization). Properties of the temperature of the downstream region of tissue 155 could be related to the pattern of energy emitted by the energy source 140 and to the flow rate of blood in the portion of subsurface vasculature 130. Further, the energy source 140 could be operated to emit energy having one or more properties related to a temperature of the downstream region of tissue 155 measured using the downstream temperature sensor 150. For example, an intensity of the emitted energy 145 emitted by the energy source 140 could be specified such that a measured temperature of the downstream region of tissue 155 is less than a specified temperature (e.g., a temperature above which blood and/or tissue experiences a coagulation, damage, or some other adverse change). An intensity of the emitted energy 145 emitted by the energy source 140 could be specified such that blood of other tissue that is heated by the emitted energy 145 does not increase in temperature above 41 degrees Celsius.

Figure 2B:
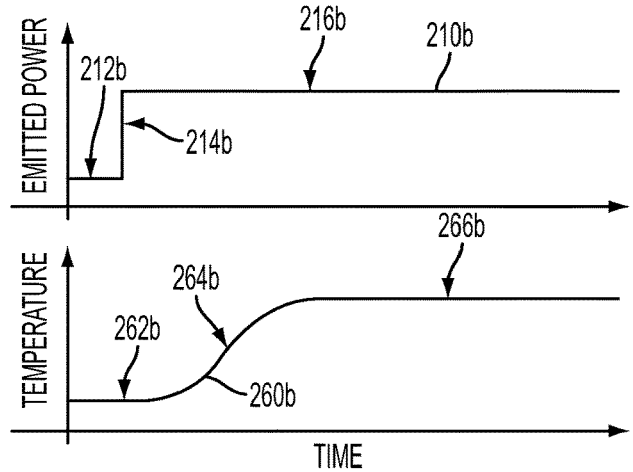
FIG. 2B illustrate example emitted energy and output waveforms that could be generated by an example flow detection system.

FIG. 2B illustrates an example emitted energy amplitude waveform 210b and an example downstream region of tissue temperature waveform 260b corresponding to a temperature profile of the downstream region of tissue 155 that could occur in response to the energy source 140 emitting energy into the portion of subsurface vasculature 130 having an amplitude profile corresponding to the example emitted energy amplitude waveform 210b. Emitted energy waveform 210a illustrates the use of the energy source 140 to emit a first energy having a first intensity 212b during a first period of time (i.e., before rising edge 214b of the emitted energy waveform 210a) and a second energy having a second intensity 216b during a second period of time (i.e., after rising edge 214b of the emitted energy waveform 210a).

The corresponding downstream temperature waveform 260b includes an initial period 262b having a first temperature, a transition period 264b, and a final period 266b having a second temperature. Before 262a the transition period 264b (i.e., before an increase in the temperature of the downstream region of tissue 155 corresponding to the rising edge 214b of the emitted energy waveform 210a), the downstream region of tissue 155 has a baseline temperature related to the environment of the downstream region of tissue 155 (e.g., an ambient temperature, metabolism of cells in or proximate to the downstream region of tissue 155, a core body temperature, a mean flow rate of blood in the portion of subsurface vasculature 130) and the value of the first intensity 212b of the energy initially emitted by the energy source 140 (e.g., an intensity of zero corresponding to the energy source 140 emitting substantially no energy before the rising edge 214b).

Properties of the transition period 264b and final period 266b could be related to a flow rate of blood in the portion of subsurface vasculature 130 and could thus be detected and/or measured in order to determine the flow rate of blood in the portion of subsurface vasculature 130. A relative timing (i.e., a time difference) between a feature of the transition period 264b and the timing of the rising edge 214b could be related to the flow rate of blood. For example, a latency or time difference between the rising edge 214b and a specified time during the transition period 264b (e.g., a time at which the temperature waveform 260b rises halfway between the temperatures of the first 262b and second 266b periods) could be related to the flow rate of blood, e.g., the flow rate could be related to a specified distance between the energy source 140 and the downstream region of tissue 155 divided by such a time difference. An absolute or relative (e.g., a difference from the temperature during the first period 262b) value of temperature during the second period 266b could be related to a flow rate of blood in the portion of subsurface vasculature 130 (e.g., a higher flow rate of blood could correspond to a lower temperature). Additional properties, features, and/or combinations thereof of the temperature (e.g., 260b) of a region of tissue downstream relative to a portion of subsurface vasculature containing blood heated by emitted energy emitted by an energy source (e.g., 210b) could be related to the flow rate of blood in the portion of subsurface vasculature.

Figure 2C:
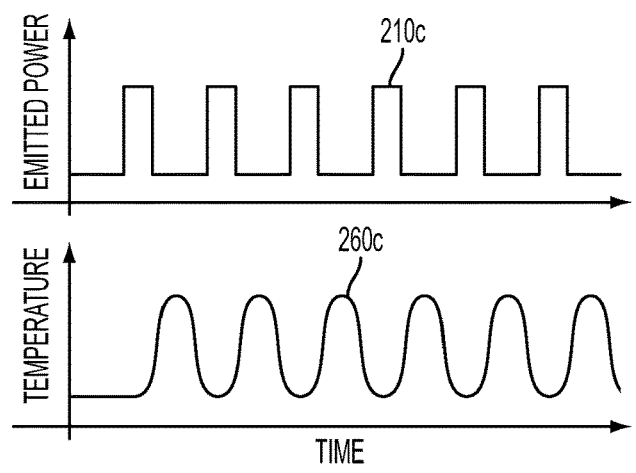
FIG. 2C illustrate example emitted energy and output waveforms that could be generated by an example flow detection system.

FIG. 2C illustrates an example emitted energy amplitude waveform 210c and an example downstream region of tissue temperature waveform 260c corresponding to a temperature profile of the downstream region of tissue 155 that could occur in response to the energy source 140 emitting energy into the portion of subsurface vasculature 130 having an amplitude profile corresponding to the example emitted energy amplitude waveform 210c. Emitted energy waveform 210c illustrates the use of the energy source 140 to emit a plurality of pulses of energy. The corresponding downstream temperature waveform 260c includes a plurality of pulses of increased temperature individually corresponding to respective individual pulses of energy in the emitted energy waveform 210c.

Properties of the plurality of pulses of increased temperature 260c could be related to a flow rate of blood in the portion of subsurface vasculature 130 and could thus be detected and/or measured in order to determine the flow rate of blood in the portion of subsurface vasculature 130. A relative timing (i.e., a time difference) between one or more features of the plurality of pulses of increased temperature 260c and respective feature(s) of the pulses of energy 210c could be related to the flow rate of blood. For example, a latency or time difference between the peaks of the pulses of increased temperature 260c and the rising edges of respective pulses of energy 210c could be related to the flow rate of blood, e.g., the flow rate could be related to a specified distance between the energy source 140 and the downstream region of tissue 155 divided by such a time difference. Respective durations of the pulses of increased temperature 260c could be related to a flow rate of blood in the portion of subsurface vasculature 130 (e.g., wider pulses of increased temperature 260c could correspond to a slower flow rate of blood). A value of temperature during one or more of the pulses of increased temperature 260c (e.g., a peak temperature, a ratio of a peak temperature over a baseline temperature) could be related to a flow rate of blood in the portion of subsurface vasculature 130 (e.g., a higher flow rate of blood could correspond to a lower peak temperature). Additional properties, features, and/or combinations thereof of pulses of increased temperature (e.g., 260c) of a region of tissue downstream relative to a portion of subsurface vasculature containing blood heated by pulses of energy (e.g., 210c) could be related to the flow rate of blood in the portion of subsurface vasculature.

The plurality of pulses of energy 210c could have a variety of properties according to a variety of applications. Individual pulses of energy of the plurality of pulses of energy 210c could have respective properties (e.g., pulse width, intensity, pulse waveform (e.g., rectangular, trapezoidal, raised cosine), wavelength). In some examples, the pulses could be substantially identical; alternatively, one or more properties of the pulses could vary between pulses according to an application. In some examples, the pulses could have a regular spacing in time (e.g., could repeat regularly and/or have a repetition frequency). For example, the pulses could repeat at a frequency that is high enough to allow determination (e.g., by measuring the temperature of the downstream region of tissue 155 at one or more points in time using the downstream temperature sensor 150) of a blood flow rate profile corresponding to the variation in blood flow rate across one or more heartbeats. The frequency of the pulses of energy could be preferentially between approximately 10 hertz and approximately 100 hertz.

Note that the illustrated example downstream region of tissue temperature waveforms (e.g., 260*a*, 260*b*, 260*c*) could be derived from one or more measurements, rather than directly reflecting a measurement made by a downstream temperature sensor. For example, the illustrated example downstream region of tissue temperature waveforms (e.g., 260*a*, 260*b*, 260*c*) could be difference waveforms related to a difference between a temperature measured by a downstream temperature sensor and a temperature measured by a further temperature sensor location elsewhere. The temperatures measured by the temperature sensors at the various locations can include a common-mode signal (e.g., a baseline body temperature of the regions of tissue surrounding the portion of subsurface vasculature). Differences between the temperatures measured at different location can reduce or eliminate the common-mode signal and provide a signal related to the heating of the blood by the energy source with a higher signal to noise ratio than would otherwise be achieved by measurement at only a single location.

Note that the movement of the illustrative heated portion of blood 160*a-c* and the corresponding downstream temperature waveform 260*a* (and other illustrative downstream temperature waveforms 260*b*, 260*c*) are meant as illustrative examples. The temperature of a region of tissue that is downstream from the location of an energy source with respect to blood flow in a portion of subsurface vasculature that can be heated by energy emitted by the energy source could have different values over time and/or be related to operation of the energy source to heat blood in the portion of subsurface vasculature in different ways than those illustrated. Further, the flow rate of blood in the portion of subsurface vasculature could affect the temperature of the downstream region of tissue (relative to the operation of the energy source) in different ways than those illustrated. The timing or other properties or features of the emitted energy waveforms (210*a-c*) and corresponding downstream portion of tissue temperature waveforms (260*a-c*) could be different from those illustrated. For example, the value, timing, or other features of the temperature of a downstream portion of tissue could change with changes in the flow rate of blood. For example, a relative timing (e.g., time difference) between pulses of energy emitted by the energy source and corresponding pulses of increased temperature of the downstream region of tissue could change from pulse to pulse with changes in the flow rate of blood in the portion of subsurface vasculature over time.

The energy source 140 could be configured in a variety of ways and include a variety of elements such that the emitted energy 145 has one or more specified properties according to an application. The emitted energy could be light energy (e.g., a beam of visible, infrared, ultraviolet, or some other type of illumination), thermal energy (e.g., heat generated by a resistive heater or some other type of heater and conducted, radiated, or otherwise transferred to the blood), acoustic energy (e.g., ultrasonic waves configured to heat the blood), and/or some other energy. The emitted energy 145 could include light having a specified wavelength and/or include light having a number of wavelengths within a specified range. In some examples, the wavelength(s) of the light (i.e., of the emitted energy 145) could be specified such that it could penetrate tissues (e.g., skin, connective tissues, the walls of a portion of subsurface vasculature), heat blood, or according to some other considerations. For example, the wavelength of the light could be between approximately 800 nanometers and approximately 850 nanometers. In some examples, a specific wavelength of light emitted by the energy source 140 could be chosen according to an availability of commodity light emitting elements within such a specified range of wavelengths. For example, the energy source 140 could include a green laser configured to emit a beam of illumination having a wavelength of approximately 532 nanometers. In some examples, the wavelength of the emitted light (i.e., of the emitted energy 145) could be specified relative to an absorption spectrum of one or more elements in blood in the portion of subsurface vasculature 130 (e.g., of hemoglobin within red blood cells in the blood) such that the emitted energy 145 preferentially heats blood in the portion of subsurface vasculature 130 relative to other elements in the environment of the portion of subsurface vasculature (e.g., skin, connective tissue, the walls of the portion of subsurface vasculature).

The energy source 140 could be selected from and/or include a wide variety of energy-emitting and/or transducing components according to an application. The energy source 140 could include an LED, a laser (e.g., gas laser, a chemical laser, a dye laser, a metal-vapor laser, a solid-state laser, a semiconductor laser), an ultrasonic emitter, a resistive heater or other contact heat source, or any other type of energy emitting element(s) configured to emit energy having one or more specified properties (e.g., intensity, wavelength) such that the energy source 140 could heat blood within a portion of subsurface vasculature to result in changes in the temperature of a downstream region of tissue 155 that could be measured by the temperature sensor 150 to determine a flow rate of blood in the portion of subsurface vasculature 130. For example, the energy source 140 could be configured to emit a beam of illumination having an energy of at least 50 milliwatts. In some applications, the energy source 140 could be configured to satisfy limited power and space requirements of the wearable device 100 such that the wearable device 100 could be battery-powered and could be comfortably worn by a wearer (e.g., a the wrist of the wearer). Additionally or alternatively, the wearable device 100 and/or other devices described herein could include an energy sink (e.g., a Peltier device, a heat pump, an element having a modulatable thermal conductivity disposed between tissues of a body and an energy sink (e.g., a reservoir of coolant)) configured to remove energy from blood in the portion of subsurface vasculature.

For example, the energy source 140 could be a small laser diode, e.g., a VCSEL, a double heterostructure laser, a quantum well laser, or some other structure of semiconductor laser incorporating gallium nitride, indium gallium nitride, aluminum gallium indium phosphide, aluminum gallium arsenide, indium gallium arsenide phosphide, lead salt, or some other material or combination of materials as a gain medium. In some examples, the energy source 140 could include frequency doublers, optics, collimators, beam modulators or some other elements according to an application. In some examples, the energy source 140 could be incorporated into other elements of the wearable device 100. For example, the energy source 140 could be wire-bonded, soldered, or otherwise electronically and/or mechanically coupled to a circuit board or other element(s) of the wearable device 100. Additionally or alternatively, the energy source 140 or elements thereof could be incorporated into a single semiconductor device (e.g., wafer or chip) with other components (e.g., an energy source power supply, a microcontroller). Further, the energy source 140 could be configured to control the direction of an emitted beam of illumination (i.e., the emitted energy 145). For example, the energy source 140 could control the direction of an emitted beam of illumination by including servos, motors, piezo elements, or other actuators configured to translate and/or rotate the energy source 140 and/or optics or other elements thereof) to enable detection of the flow rate of blood in specified sub-regions of the portion of subsurface vasculature 130 by directing the beam of illumination (i.e., the emitted energy 145) toward the different specified sub-regions of the portion of subsurface vasculature 130. In some examples, this could be performed to adjust a distance between a region of the subsurface vasculature 130 containing blood that is being heated by the energy source 140 and the location of the downstream region of tissue 155 whose temperature can be measured by the downstream temperature sensor 150.

In some examples, the wearable device 100 could include more than one energy source. Individual energy sources of the more than one energy source could have respective specified properties (e.g., locations, intensities of emitted energies) according to an application. More than one energy source could be provided to allow for detection of blood flow rate in more than one region of the portion of subsurface vasculature 130 and/or in other portions of subsurface vasculature in the arm of the wearer. More than one energy source could be provided to detect of the flow rate of blood when the location of the portion of subsurface vasculature relative to the more than one energy source and/or other elements of the wearable device 100 is unknown and/or not controlled or control-able by elements of the wearable device 100. For example, a plurality of energy sources could be disposed in the wearable device 100 in a linear array oriented perpendicular to the long axis of the arm of the wearer. One or more individual energy sources of the linear array of energy sources could be positioned such that the one or more individual energy sources could emit energy to heat blood in the portion of subsurface vasculature 130. The one or more individual energy sources could be operated to emit such energies to heat the blood while the other energy sources are not operated to emit such energies and/or are operated according to some other application.

The temperature sensor 150 could include any variety of temperature-detecting apparatus configured to measure a temperature of a downstream region of tissue (i.e., a region of tissue that is downstream from the first location 143 with respect to blood flow in the portion of subsurface vasculature 130, e.g., 155) via the second location 153 (e.g., by being in thermal contact with skin at the second location 153, by receiving infrared radiation through the second location 153). The second location 153 could be a specified distance from the first location 143 such that a flow rate of blood in the portion of subsurface vasculature 130 could be determined based on the specified distance and measurements made using the temperature sensor 150 (e.g., a blood flow rate could be related to the specified distance divided by a time difference between a feature of a measured temperature of the downstream region of tissue 155 and timing of operation of the energy source 140 (e.g., the timing of a rising edge of a pulse of emitted energy)). For example, the first location 143 and the second location 153 could be separated by a distance of between approximately 1 millimeter and approximately 5 millimeters.

The temperature sensor 150 could include one or more photodetectors, photodiodes, phototransistors, CCDs, active pixel sensors, photoresistors, or other infrared-light-sensitive elements. The temperature sensor 150 could be config- ured to detect an intensity, a wavelength, a spectrum, or some other property of infrared light emitted by the downstream region of tissue 155 related to the temperature of the downstream region of tissue 155 and received at one or more locations on or within the temperature sensor 150. In some examples, the temperature sensor 150 could include an infrared camera (e.g., an aperture, a plurality of individual light-sensitive elements (e.g., a CCD, an array of active pixel sensors), and/or optics).

A temperature sensor (e.g., 150) configured to receive infrared light could include a variety of optical components according to an application. The temperature sensor 150 could include lenses, polarization filters, color filters, apertures, mirrors, diffraction gratings, liquid crystal elements, baffles, or other optical elements to affect the infrared light received by the temperature sensor 150. In some examples, the temperature sensor 150 could include a color filter configured to substantially block light having wavelengths similar to a wavelength of light emitted by the energy source 140. In some examples, the temperature sensor 150 could include a color filter configured to substantially block light having wavelengths other than wavelengths within a specified range of infrared wavelengths. In some examples, the temperature sensor 150 could include an aperture, lenses, or other element(s) configured to make the temperature sensor 150 selectively sensitive to infrared light coming from a particular direction(s) and/or location(s) relative to the temperature sensor 150, energy source 140, or other elements of the wearable device 100. For example, the temperature sensor 150 could be configured to be selectively sensitive to infrared light emitted from a specified downstream (or other) region of tissue (e.g., 155).

Additionally or alternatively, the temperature sensor 150 could include a temperature-sensitive element (i.e., an element having one or more electrical properties related to the temperature of the element) in thermal contact with the second location 153 (i.e., in direct or indirect physical contact with the second location 153 such that the temperature of the temperature-sensitive element corresponds to the temperature of a downstream region of tissue via heat conduction through the second location 153). Temperature-sensitive elements could include thermistors, thermocouples, resistance temperature detectors, quartz thermometers, silicon bandgap temperature sensors, or some other temperature sensitive elements and/or combinations of temperature sensitive elements. Such temperature-sensitive elements could be disposed in the wearable device 100 such that they are in direct thermal contact with skin at the second location 153 (i.e., could be disposed on an external surface of the housing 110). Additionally or alternatively, an element having a specified thermal conductivity (e.g., a metal rod) could be disposed in the wearable device 100 to contact skin at the second location 153 and to contact the temperature-sensitive element. For example, the thermally-conductive element could be a rounded metal pin configured to protrude from the housing 110 and to contact skin at the second location 153, and the temperature-sensitive element could be disposed on the thermally-conductive element. A thermally-conductive element could be spring-loaded, have a coating, and/or have a specified geometry to ensure consistent contact with skin of a wearer.

In some examples, the wearable device 100 could include more than one temperature sensor (e.g., a plurality of temperature sensors) disposed at more than one location relative to the energy source 140, portion of subsurface vasculature 130, or other elements of an environment of interest. The more than one temperature sensor could be provided to allow for detection of a blood flow in more than one region of the arm of the wearer (e.g., multiple locations and/or branches of the portion of subsurface vasculature 130). The more than one temperature sensor could be provided to enable higher-accuracy or otherwise improved detection of blood flow in the portion of subsurface vasculature. For example, the temperatures measured by a downstream temperature sensor and a further temperature sensor located elsewhere could include a first, common-mode signal (e.g., a baseline body temperature of the regions of tissue surrounding the portion of subsurface vasculature 130), and the temperature measured by the downstream temperature sensor could further include a second signal related to the heating of the blood by the energy source 140. The difference between the temperature measurements obtained by the temperature sensors at different locations can provide a signal related to the heating of the blood by the energy source that has a higher signal to noise ratio than would otherwise be achieved by measuring the temperature at only one location.

For example, the wearable device 100 could include an upstream temperature sensor configured to measure a temperature of an upstream region of tissue (i.e., a region of tissue upstream from the first location 143 with respect to blood flow in the portion of subsurface vasculature 130). Upstream temperatures measured by the upstream temperature sensor could be used to offset temperatures measured by the downstream temperature sensor 150 (e.g., to remove a 'baseline' component from the temperature measured by the downstream temperature sensor 150, leaving components of the temperature of the downstream region of tissue 153 that are related to the operation of the energy source 140 to heat blood in the portion of subsurface vasculature 130) or to determine a blood flow or some other property (e.g., a body temperature, a thermal conductivity of blood and/or other tissues of the wearer) of the wearer.

An additional temperature sensor could be disposed at a specified location relative to the energy source 140 and could be used to measure the temperature of a corresponding region of tissue. The measured temperature could be used to determine a thermal property of tissue of the wearer (e.g., a thermal conductivity of the tissue, by determining a rate of change of other property of the measured temperature relative to operation of the energy source 140 to heat blood in the portion of subsurface vasculature 130). Further, the energy source 140 could be operated responsive to temperatures measured using the additional temperature sensor (e.g., an intensity of the emitted energy 145 emitted by the energy source 140 could be maintained below a determined level related to a temperature measured by the additional temperature sensor such that the temperature of blood and/or other tissue of the wearer does not increase above a specified temperature, e.g., 41 degrees Celsius).

In some embodiments, the wearable device 100 could include a plurality of temperature sensors arranged in a linear array or according to some other specified geometry (e.g., a rectangular or other two-dimensional array). Such an array of temperature sensors could include the downstream temperature sensor 150 or some other temperature sensor (e.g., an upstream temperature sensor) of the wearable device 100. A linear array of temperature sensors could be arranged perpendicular to the direction of the portion of subsurface vasculature 130 such that, when the wearable device 100 is mounted to a wrist or other protruding element of a wearer (e.g., an ankle, a leg, an arm), at least one temperature sensor of the linear array is positioned to measure temperature of the downstream region of tissue 155. An array of temperature sensors could additionally or alternatively be configured and/or operated according additional applications. For example, an array of temperature sensors (and/or an infrared camera, e.g., a camera configured to detect light having near-infrared wavelengths between approximately 750 nanometers and approximately 900 nanometers) could allow a map or image of one or more thermal properties of tissue of the wearer to be determined. Such imaging could be further facilitated by appropriate illumination of the tissues in the environment of the portion of subsurface vasculature, for example, by illuminating the tissues with near-infrared light (e.g., light having wavelengths between approximately 750 nanometers and approximately 900 nanometers). For example, locations, branching patterns, widths, or other information about one or more portions of subsurface vasculature (e.g., 130) of the wearer could be determined (e.g., by detecting a difference and/or change in temperature corresponding to portions of vasculature that is different than such corresponding to other types of tissue). Further, such thermal mapping information could be used to determine the flow rate of blood in the portion of subsurface vasculature 130.

The controller of the wearable device 100 being configured to operate the energy source 140 and the downstream temperature sensor 150 to determine a flow rate of blood in the portion of subsurface vasculature 130 could include a variety of different methods or modes of operation of the energy source 140, the downstream temperature sensor 150, and/or additional components. The controller could operate the energy source 140 to emit energies (e.g., 145) having respective properties (e.g., intensities) during respective periods of time. The controller could operate the downstream temperature sensor 150 to measure the temperature of a downstream region of tissue (e.g., 155) via the second location 153 at one or more points in time relative to the timing of operation of the energy source 140 (e.g., relative to one or more or the respective periods of time and/or transitions between such).

The controller could operate the downstream temperature sensor 150 (or some other temperature sensor of the wearable device 100) to measure a temperature at a plurality of points in time to determine a temperature waveform of a downstream region of tissue (or of some other region of tissue) over time. Such operation could be continuous (i.e., the controller could sample the temperature at regular intervals or according to some other pattern in time) or could occur during specified periods of time (e.g., a period of time extending from a specified time before operation of the energy source 140 to emit a heating energy to a specified time after the energy source 140 ceases to emit the energy). Alternatively, some operating modes of the wearable device 100 could include using the downstream temperature sensor to measure a temperature at a single point in time relative to the timing of the operation of the energy source 140.

Operating a temperature sensor (e.g., 150) to measure a temperature could include using an analog-to-digital convertor (ADC) to measure an electrical output (a voltage, a current) and/or an electrical property (e.g., a resistance) of the temperature sensor. Additionally or alternatively, one or more comparators, amplifiers, rectifiers, filters, or other electronic elements could be coupled to the temperature sensor and using the temperature sensor to measure a temperature could include measuring and/or detecting an output of one or more of the electronic elements coupled to the temperature sensor (e.g., detecting a digital output of a comparator to measure whether the temperature is above or below a specified temperature related to the configuration of the comparator and/or other elements).

Operating the energy source 140 to emit energy and to heat blood in the portion of subsurface vasculature 130 could include emitting energies having a variety of specified properties over time according to a variety of applications. The intensity, wavelength, spectral profile, or other properties of the emitted energy could be controlled. Further, the direction, beam width, focus, or other properties of an emitted beam of illumination (or other directed form of emitted energy) could be controlled such that the location of the blood being heated by the energy source 140 can be controlled.

The energy source 140 could be operated to emit a first energy having a first intensity during a first period of time and to emit a second energy having a second intensity during a second period of time. This could include operating the energy source 140 to emit one or more pulses of energy during respective periods of time and having respective properties (e.g., intensities, pulse widths, pulse waveforms (e.g., square pulses, trapezoidal pulses)). This could include continuously varying one or more properties of the energy emitted by the energy source 140 (e.g., emitting en energy having a sinusoidal-varying intensity). Determining a flow rate of blood in such examples could include determining a relative timing between a temporal feature (e.g., a rising edge of a pulse of energy, a time of transition between a first period of time and a second period of time during which energies having respective intensities are emitted) of the output (i.e., of any emitted energies) of the energy source 140 and a feature of a temperature waveform and/or the timing of a temperature measurement made using a temperature sensor (e.g., 150). For example, a flow rate of blood could be determined by dividing a distance between the energy source 140 and the downstream temperature sensor 150 (i.e., a distance between the first location 143 and the second location 153) by a measured and/or determined time difference between a temporal feature of the output of the energy source 140 (e.g., a rise time of a pulse of energy) and a feature of a temperature waveform measured using the downstream temperature sensor 140 (e.g., a rising edge of a pulse of increased temperature in the measured temperature waveform). The distance between the first 143 and second 153 locations could be a specified distance, e.g., between approximately 1 millimeter and approximately 5 millimeters.

The energy source 140 could be operated to emit a plurality of pulses of energy having a regular spacing in time, i.e., at a specified frequency. The specified frequency could be between approximately 10 hertz and approximately 100 hertz. The frequency could be specified such that a plurality of time differences determined between respective pulses and corresponding respective features in a measured temperature waveform of the downstream region of tissue (e.g., 155) could be used to determine a respective plurality of blood flow rates corresponding to a plurality of specified points in time (e.g., time points of rising edges or other temporal features of the pulses of energy). Additionally or alternatively, the measured temperature waveform, the plurality of determined blood flow rates, the plurality of determined time differences, or some other related information could be filtered (by some analog electronics of the wearable device 100 and/or by a digital filter implemented by the controller) to determine a blood flow rate that had a lower noise, higher accuracy, or some other improved property relative to a blood flow rate determined using information related to a single pulse of energy and corresponding temperature waveform feature (e.g., measured pulse of increased temperature).

The controller could be configured to operate additional temperature sensors to determine blood flow rate in the portion of subsurface vasculature 130 and/or to determine other information. For example, the controller could operate a further temperature sensor to measure a temperature of a further region of tissue that is not downstream, and could determine a blood flow rate in the portion of subsurface vasculature 130 based on a difference between the temperature measured by the further temperature sensor and a temperature measured using the downstream temperature sensor 150. In some embodiments, the further temperature sensor could be an upstream temperature sensor disposed at a location opposite the energy source 140 from the downstream temperature sensor 150 such that subtracting the temperature measured by the upstream temperature sensor from the temperature measured by the downstream temperature sensor 150 could result in a determined temperature relating substantially to convective heat transfer effects of flowing blood in the portion of subsurface vasculature 130 and substantially not related to conductive heat transfer effects of the tissue of the wearer. That is, any changes in the temperature measured by the downstream temperature sensor due to conductive heat transfer effects of the tissue will be substantially similar to changes in the temperature measured by the further (i.e., upstream) temperature sensor due to conductive heat transfer effects of the tissue.

Additionally or alternatively, a thermal property (e.g., a thermal conductivity, a heat capacity) of a further region of tissue of the wearer (i.e., a region of tissue whose temperature can be measured by the further temperature sensor) could be determined. In some examples, the energy source 140 could emit a first energy having a first intensity during a first period of time and a second energy having a second intensity during a second period of time, and the thermal property could be determined based on the first intensity, the second intensity, a temperature measured by the further temperature sensor at a specified point in time, and the timing of the first and second periods of time relative to the specified point in time.

Further, the controller could be configured to determine a pressure of blood in the portion of subsurface vasculature 130 based on at least one determined flow rate of blood in the portion of subsurface vasculature. For example, the pressure of blood could be determined by using a lookup table of other such function to determine a pressure corresponding to a determined blood flow rate. Additionally or alternatively, the pressure of blood could be determined based on the determined blood flow rate using a model or other functions based on some information about the blood (e.g., a viscosity, a density), the portion of subsurface vasculature 130 (e.g., a diameter, an internal drag coefficient), or other tissue of the wearer. Calibration data (e.g., parameters, calibration curves) about models, functions, lookup tables, or other algorithms used to determine a blood pressure based on a determined blood flow rate could be input into the wearable device 100 (e.g., using a user interface of the wearable device and/or a user interface of some other system in communication with the wearable device 100) by the wearer or by some other user (e.g., a physician).

Additionally or alternatively, the calibration data could be determined through a calibration procedure whereby one or more detected values of blood flow rate (detected, e.g., by the wearable device 100) could be associated with corresponding one or more values of blood pressure. The values of blood pressure could be measured using a sphygmomanometer or other apparatus configured to directly measure blood pressure in the portion of subsurface vasculature 130. Such a pressure measurement apparatus could be part of the wearable device 100 or could be part of some other device. In some examples, calibration data could be generated by detecting one or more blood flow rates when the portion of subsurface vasculature 130 is elevated to two or more different elevations relative to the heart of the body containing the portion of surface vasculature. That is, the portion of subsurface vasculature 130 (and related tissues, e.g., the wearer's hand and wrist) could be elevated to a first elevation and at least one blood flow rate could be determined using the wearable device 100. The portion of subsurface vasculature 130 could then be elevated to a second elevation and at least one blood flow rate could be determined using the wearable device 100. The calibration data could then be determined based on the at least one blood flow rate determined when the portion of subsurface vasculature 130 is at the first elevation, on the at least one blood flow rate determined when the portion of subsurface vasculature 130 is at the second elevation, and a difference between the first and second elevations. For example, the respective at least one blood flow rates determined at the first and second elevations could be maximum blood flow rates corresponding to points in respective heartbeats corresponding to a systolic blood pressure in the portion of subsurface vasculature 130. The difference between a systolic blood pressure when the portion of subsurface vasculature is at the first elevation and a systolic blood pressure when the portion of subsurface vasculature is at the second elevation could be related to a difference in pressure corresponding to a difference in elevation in a water column (or column of other fluid having a density similar to the wearer's blood) substantially equal to the difference between the first and second elevations. Thus, a difference in the maximum blood flow rates corresponding to the difference in pressure determined using the difference between the first and second elevations could be used to determine the calibration data. Such elevation-change-related calibration processes could be performed continuously (e.g., an accelerometer or other displacement and/or location sensor of the wearable device 100 could be used to continuously determine changes in elevation of the portion of subsurface vasculature, allowing the calibration data to be repeatedly refined and/or updated).

Note that the detection of the flow rate of blood in a portion of subsurface vasculature 130 based on the movement of heated portions of blood (e.g., illustrative heated portion of blood 160a-c) heated by an emitted energy (e.g., 145) emitted by the energy source 140 in the portion of subsurface vasculature 130 and the detection of a related level and/or change in temperature of a downstream region of tissue (e.g., 155) by the downstream temperature sensor 150 is intended as a non-limiting illustrative example of the detection of flow rates of fluids in an environment of interest. For example, the environment could be any tissue of a human (e.g., an ankle, an ear, a neck, a portion of central vasculature) or animal, and the fluid could be any fluid of the human or animal body (e.g., arterial blood, capillary blood, venous blood, lymph, interstitial fluid, stomach or other digestive contents, air in the airways and/or lungs, cerebrospinal fluid) that can be heated by an emitted energy such that the movement of a resulting heated portion of the fluid can be detected and related to the flow of the fluid. The environment could be an in vivo biological environment (e.g., a tissue of a living human, animal, plant, etc.) or an in vitro environment. The environment could be a biological sample in a sample container, cuvette, pipette, microscope slide, or other vessel. The fluid could be part of a biological or chemical process. For example, the fluid could be a fluid in a water treatment process, a fluid in a food or drug preparation process, a lake, stream, or river in a natural environment, or some other fluid in some other environment. The fluid could be a liquid, a gel, a gas, or some other phase of flowing matter or combination of phases (e.g., an emulsion).

III. Example Devices

Figure 3:
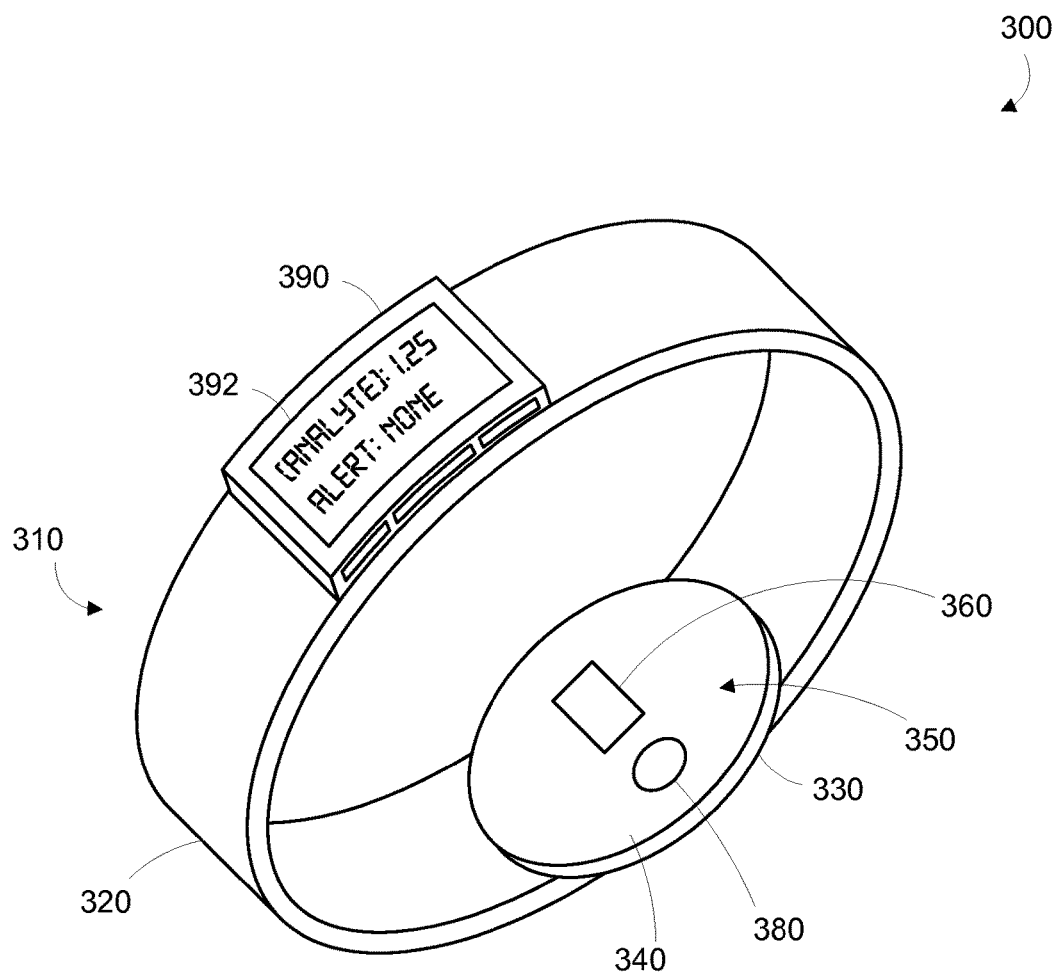
FIG. 3 is a perspective view of an example wearable device.

A wearable device 300 (illustrated in FIG. 3) can automatically measure a flow rate of blood in a portion of subsurface vasculature of a person wearing the device. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount 310, such as a belt, wristband, ankle band, etc. can be provided to mount the device at, on or in proximity to the body surface. The mount 310 may prevent the wearable device from moving relative to the body to reduce measurement error and noise. In one example, shown in FIG. 3, the mount 310, may take the form of a strap or band 320 that can be worn around a part of the body. Further, the mount 310 may be an adhesive substrate for adhering the wearable device 300 to the body of a wearer.

A measurement platform 330 is disposed on the mount 310 such that it can be positioned on the body where subsurface vasculature is easily observable. An inner face 340 of the measurement platform is intended to be mounted facing to the body surface. The measurement platform 330 may house a data collection system 350, which may include at least one energy source 380 configured to emit energy into a portion of subsurface vasculature through the external body surface at a first location. The measurement platform 330 additionally includes at least one temperature sensor 360 configured to detect the temperature of a downstream region of tissue (i.e., a region of tissue that is downstream from the first location with respect to blood flow in the portion of subsurface vasculature) via the external body surface at a second location. The wearable device 300 additionally includes a controller (not shown) configured to operate the energy source 380 and the temperature sensor 360 to determine a flow rate of blood in the portion of subsurface vasculature.

The data collection system 350 may additionally include additional detectors for detecting other physiological parameters, which could include any parameters that may relate to the health of the person wearing the wearable device. For example, the data collection system 350 could include detectors configured to measure blood pressure, pulse rate, respiration rate, skin temperature, etc. In a non-exhaustive list, additional detectors may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. The additional detectors could be additional temperature sensors. In some examples, the additional sensors could be configured to measure the temperature of upstream regions of tissue or other regions of tissue to enable detection of the blood flow rate in the portion of subsurface vasculature and/or to determine a blood flow rate in a different portion of subsurface vasculature of the wearer. In some examples, a plurality of temperature sensors and/or a camera configured to detect near-infrared light (e.g., light having wavelengths between approximately 750 nanometers and approximately 900 nanometers) could be included to detect a temperature map of tissue of the wearer, to determine a location, diameter, branching pattern, to determine a flow rate of blood in the portion of subsurface vasculature, or other information about the portion of subsurface vasculature, or to allow for some other application of the wearable device 300.

The energy source 380 is configured to emit an energy that can penetrate the wearer's skin into the portion of subsurface vasculature, for example, into a lumen of the subsurface vasculature. The emitted energy can be any kind of energy that is benign to the wearer and that results at least in heating of a portion of blood in the portion of subsurface vasculature such that the temperature sensor 360 can be operated to detect a temperature of a downstream region of tissue that can be used to determine the flow rate of blood in the portion of subsurface vasculature. The emitted energy could be a light energy (e.g., a beam of visible, infrared, ultraviolet, or some other type of illumination), a thermal energy (e.g., heat generated by a resistive heater or some other type of heater and conducted, radiated, or otherwise transferred to the blood), an acoustic energy (e.g., ultrasonic waves configured to heat the blood), or some other energy. The wavelength of emitted illumination (i.e., of emitted energy including light) could be specified to penetrate biological tissues of a wearer; for example, the emitted illumination could have a wavelength within a near-infrared (NIR) transparency window of biological tissue. The wavelength of the emitted illumination could be specified to be a wavelength that is absorbed and converted into heat by blood cells, such as a wavelength between approximately 800 nanometers and approximately 850 nanometers.

The wearable device 300 may also include a user interface 390 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 390 may include a display 392 where a visual indication of the alert or recommendation may be displayed. The display 392 may further be configured to provide an indication of the measured physiological parameters, for instance, a determined flow rate of blood in a portion of subsurface vasculature.

Figure 4A:
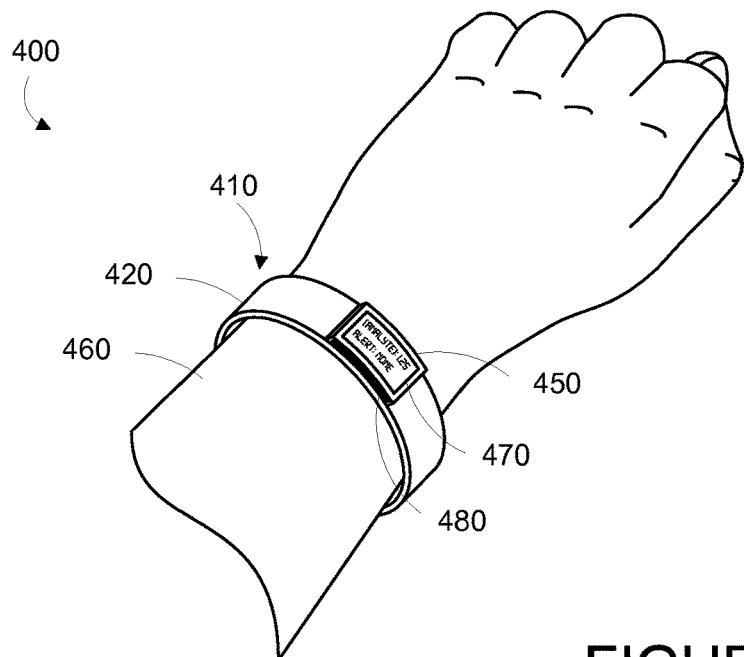
FIG. 4A is a perspective top view of an example wrist-mounted device, when mounted on a wearer's wrist.
Figure 4B:
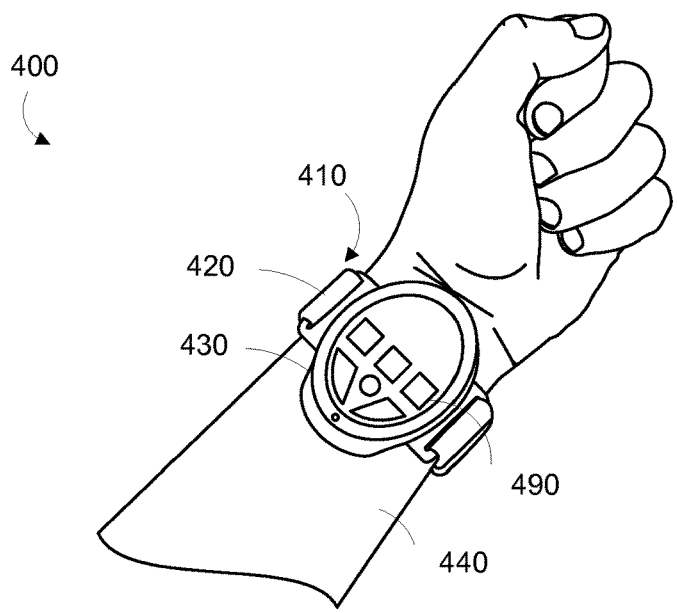
FIG. 4B is a perspective bottom view of an example wrist-mounted device shown in FIG. 4A, when mounted on a wearer's wrist.

In some examples, the wearable device is provided as a wrist-mounted device, as shown in FIGS. 4A, 4B, and 5A-5C. The wrist-mounted device may be mounted to the wrist of a living subject with a wristband or cuff, similar to a watch or bracelet. As shown in FIGS. 4A and 4B, the wrist mounted device 400 may include a mount 410 in the form of a wristband 420, a measurement platform 430 positioned on the anterior side 440 of the wearer's wrist, and a user interface 450 positioned on the posterior side 460 of the wearer's wrist. The wearer of the device may receive, via the user interface 450, one or more recommendations or alerts generated either from a remote server or other remote computing device, or alerts from the measurement platform.

Such a configuration may be perceived as natural for the wearer of the device in that it is common for the posterior side 460 of the wrist to be observed, such as the act of checking a wrist-watch. Accordingly, the wearer may easily view a display 470 on the user interface. Further, the measurement platform 430 may be located on the anterior side 440 of the wearer's wrist where the subsurface vasculature may be readily observable. However, other configurations are contemplated.

The display 470 may be configured to display a visual indication of the alert or recommendation and/or an indication of the measured physiological parameters, for instance, the flow rate and/or a pressure of blood in a portion of subsurface vasculature of the wearer. Further, the user interface 450 may include one or more buttons 480 for accepting inputs from the wearer. For example, the buttons 480 may be configured to change the text or other information visible on the display 470. As shown in FIG. 4B, measurement platform 430 may also include one or more buttons 490 for accepting inputs from the wearer. The buttons 490 may be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

Figure 5A:
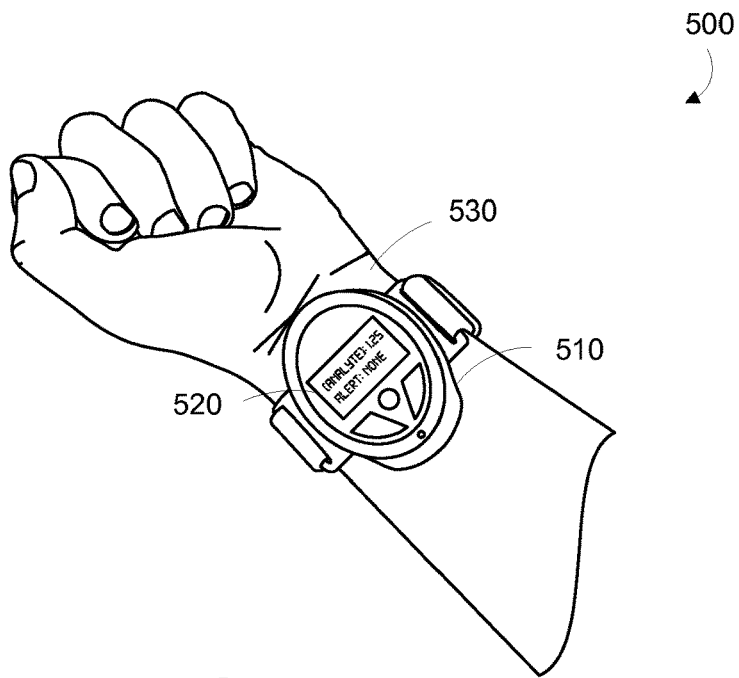
FIG. 5A is a perspective bottom view of an example wrist-mounted device, when mounted on a wearer's wrist.
Figure 5B:
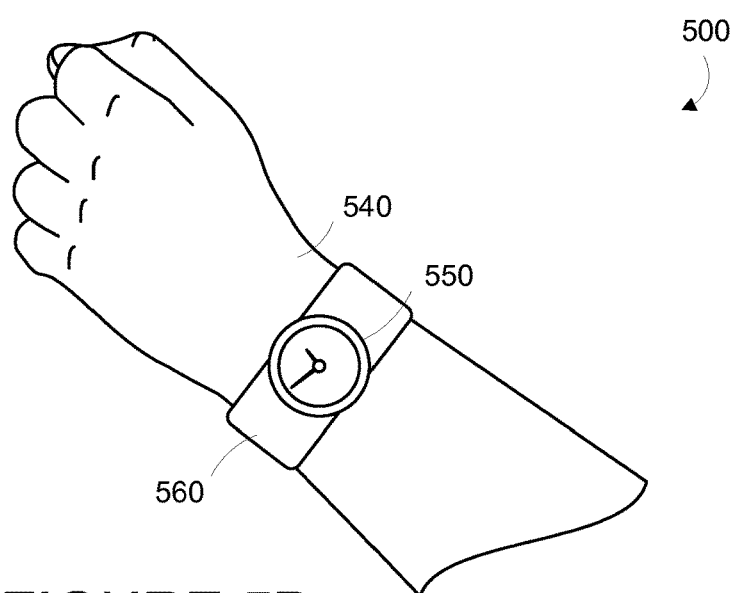
FIG. 5B is a perspective top view of an example wrist-mounted device shown in FIG. 5A, when mounted on a wearer's wrist.
Figure 5C:
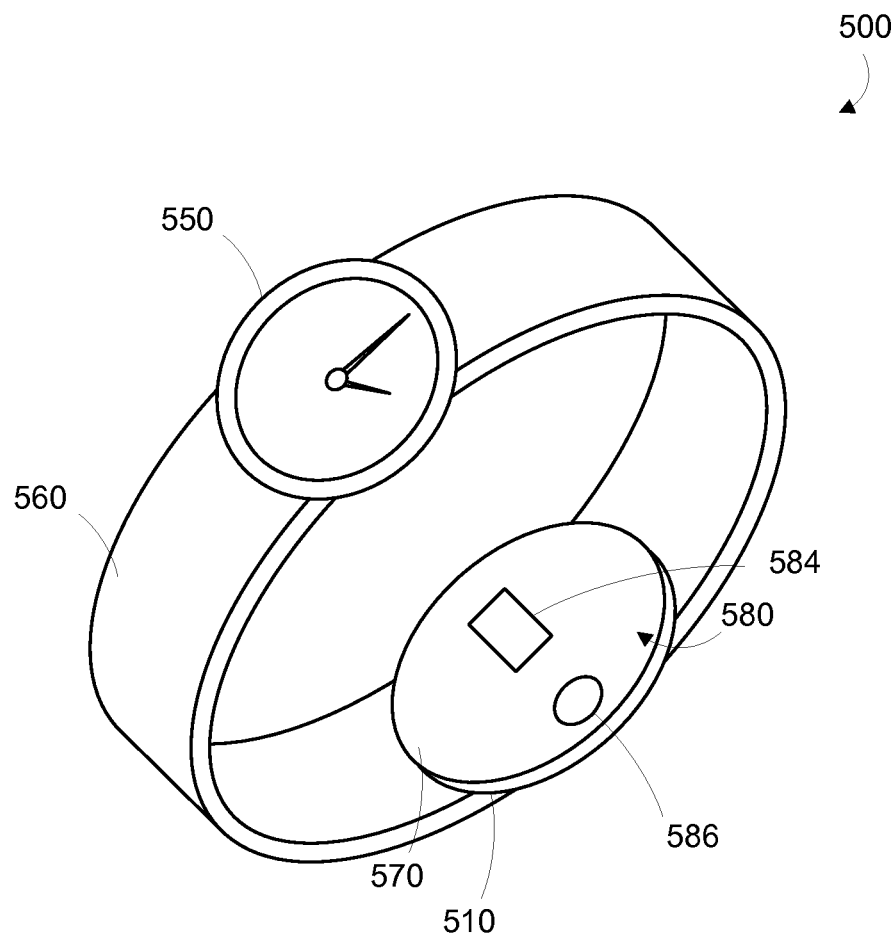
FIG. 5C is a perspective view of an example wrist-mounted device shown in FIGS. 5A and 5B.

In another example wrist-mounted device 500, shown in FIGS. 5A-5C, the measurement platform 510 and user interface 520 are both provided on the same side of the wearer's wrist, in particular, the anterior side 530 of the wrist. On the posterior side 540, a watch face 550 may be disposed on the strap 560. While an analog watch is depicted in FIG. 5B, one of ordinary skill in the art will recognize that any type of clock may be provided, such as a digital clock. As can be seen in FIG. 5C, the inner face 570 of the measurement platform 510 is intended to be worn proximate to the wearer's body. A data collection system 580 housed on the measurement platform 510 may include an energy source 586 and temperature sensor 584.

FIG. 6 is a simplified schematic of a system including one or more wearable devices 600. The one or more wearable devices 600 may be configured to transmit data via a communication interface 610 over one or more communication networks 620 to a remote server 630. In one embodiment, the communication interface 610 includes a wireless transceiver for sending and receiving communications to and from the server 630. In further embodiments, the communication interface 610 may include any means for the transfer of data, including both wired and wireless communications. For example, the communication interface may include a universal serial bus (USB) interface or a secure digital (SD) card interface. Communication networks 620 may be any one of may be one of: a plain old telephone service (POTS) network, a cellular network, a fiber network and a data network. The server 630 may include any type of remote computing device or remote cloud computing network. Further, communication network 620 may include one or more intermediaries, including, for example wherein the wearable device 600 transmits data to a mobile phone or other personal computing device, which in turn transmits the data to the server 630.

In addition to receiving communications from the wearable device 600, such as collected physiological parameter data and data regarding health state as input by the user, the server may also be configured to gather and/or receive either from the wearable device 600 or from some other source, information regarding a wearer's overall medical history, environmental factors and geographical data. For example, a user account may be established on the server for every wearer that contains the wearer's medical history. Moreover, in some examples, the server 630 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the physiological parameter data and the indicated health state of the user. From this information, the server may be configured to derive an indication of the effectiveness of the drug or treatment. For example, if a drug is intended to treat nausea and the wearer of the device does not indicate that he or she is experiencing nausea after beginning a course of treatment with the drug, the server may be configured to derive an indication that the drug is effective for that wearer. In another example, a wearable device may be configured to measure blood glucose. If a wearer is prescribed a drug intended to treat diabetes, but the server receives data from the wearable device indicating that the wearer's blood glucose has been increasing over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

IV. Example Electronics Platform for a Device

Figure 7:
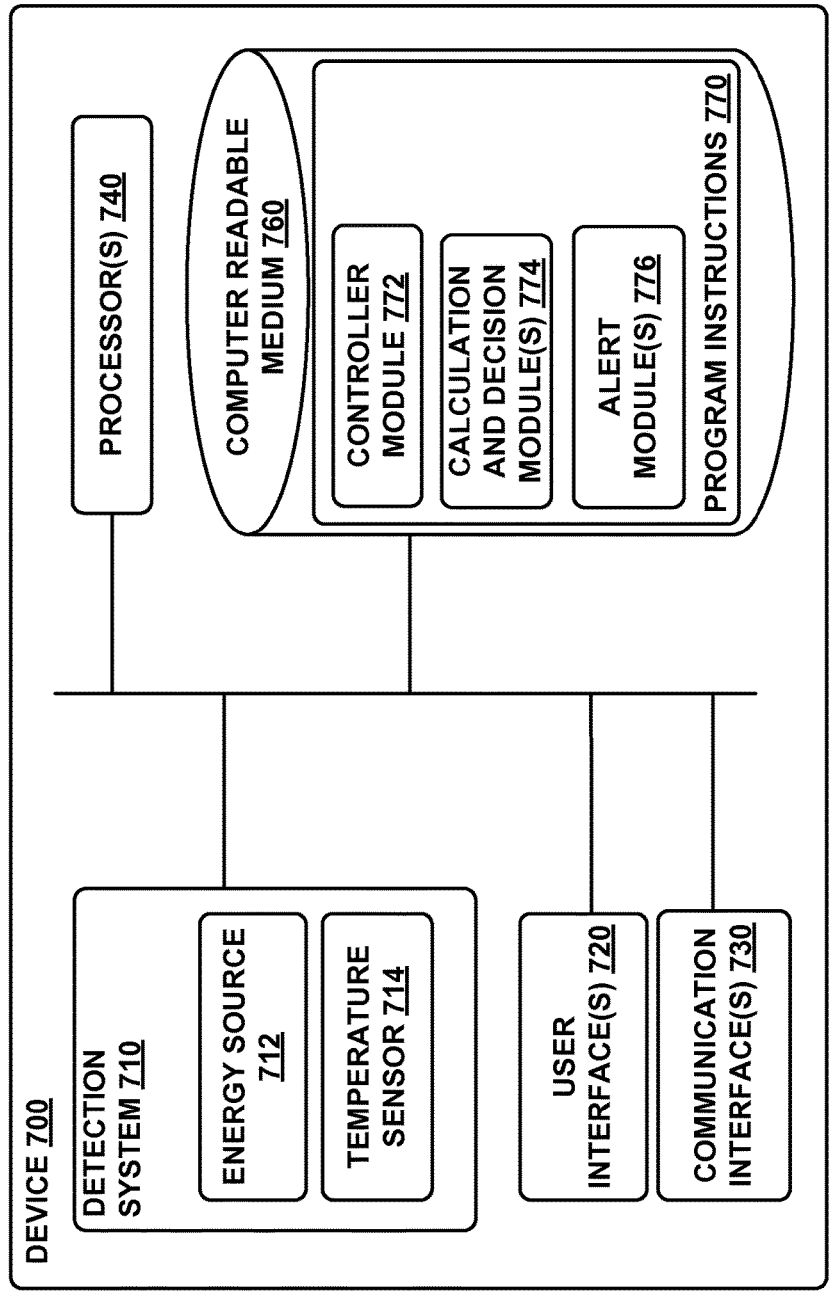
FIG. 7 is a functional block diagram of an example device.

FIG. 7 is a simplified block diagram illustrating the components of a device 700, according to an example embodiment. Device 700 may take the form of or be similar to one of the wrist-mounted devices 100, 300, 400, 500, 600 shown in FIGS. 1, 3, 4A-B, and 5A-5C. However, device 700 may also take other forms, such as an ankle, waist, or chest-mounted device. Device 700 could also take the form of a device that is not configured to be mounted to a body. For example, device 700 could take the form of a handheld device configured to be maintained in proximity to an environment of interest (e.g., a body part, a biological sample container, a volume of a water treatment system) by a user or operator of the device 700 or by a frame or other supporting structure. Device 700 could also take the form of a device configured to heat (by emitting energy) a specified region within and to detect the temperature at one or more locations in an in vitro biological environment or some other environment, for example, a fluid volume within a water treatment process. Device 700 also could take other forms.

In particular, FIG. 7 shows an example of a device 700 having a detection system 710, a user interface 720, communication interface 730 for transmitting data to a remote system, processor 740, and a computer readable medium 760. The components of the device 700 may be disposed on a mount or on some other structure for mounting the device to enable stable detection of a flow rate of fluid in an environment of interest, for example, to an external body surface where a portion of subsurface vasculature is readily observable.

Processor 740 may be a general-purpose processor or a special purpose processor (e.g., digital signal processors, application specific integrated circuits, etc.). The one or more processors 740 can be configured to execute computer-readable program instructions 770 that are stored in the computer readable medium 760 and that are executable to provide the functionality of a device 700 described herein.

The computer readable medium 760 may include or take the form of one or more non-transitory, computer-readable storage media that can be read or accessed by at least one processor 740. The one or more computer-readable storage media can include volatile and/or non-volatile storage components, such as optical, magnetic, organic or other memory or disc storage, which can be integrated in whole or in part with at least one of the one or more processors 740. In some embodiments, the computer readable medium 760 can be implemented using a single physical device (e.g., one optical, magnetic, organic or other memory or disc storage unit), while in other embodiments, the computer readable medium 760 can be implemented using two or more physical devices.

Detection system 710 includes a temperature sensor 714 and an energy source 712. The energy source 712 is configured to emit energy into an environment of interest to heat a portion of the environment of interest (e.g., a portion of blood in a portion of subsurface vasculature). The detection system 710 additionally includes at least one temperature sensor 714 configured to detect the temperature of a region of the environment of interest. In a non-exhaustive list, the temperature sensor 714 may include one or more of an infrared-sensitive photodiode, an infrared-sensitive phototransistor, an infrared-sensitive photoresistor, an infrared-sensitive active pixel sensor, an infrared-sensitive CCD, an infrared camera, or some other infrared light sensitive element configured to measure the temperature of a region of interest. Additionally or alternatively, the temperature sensor 714 could be in thermal contact with the environment of interest and could include a thermistor, a thermocouple, a silicon bandgap thermometer, or some other-temperature-sensitive element. In some examples, the detection system 710 could include additional temperature sensors (e.g., a linear or otherwise configured array of temperature sensors configured to measure the temperature of a corresponding set of regions within the environment of interest).

The detection system 710 may additionally include additional detectors for detecting physiological parameters of a human whose body includes the environment of interest (e.g., the environment of interest is a portion of subsurface vasculature of the human), which could include any parameters that may relate to the health of the person being measured by the device 700. For example, the detection system 710 could include detectors configured to measure blood pressure, pulse rate, respiration rate, skin temperature, etc. In a non-exhaustive list, additional detectors may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor.

The detection system 710 could additionally include electronics configured to operate the energy source 712 and the temperature sensor 714. The electronics could include an analog-to-digital converter (ADC) configured to sample an output (e.g., a voltage, a current) of the temperature sensor 714 and/or of electronics coupled to the temperature sensor 714 (e.g., a resistance sensing circuit, a transimpedance amplifier) at one or more points in time such that a flow rate of fluid in the environment of interest (e.g., a flow rate of blood in a portion of subsurface vasculature) could be determined. For example, the ADC could be operated to sample an electrical signal related to the temperature sensor 714 at a specified rate (e.g., one kilohertz) to detect a temperature waveform and/or some other property of the temperature of a region of the environment of interest. Additionally or alternatively, the electronics could include one or more comparators or other electronic components configured to produce one or more electronic signals related to the temperature sensor 714 that could be used to determine a flow rate of fluid in the environment of interest.

The program instructions 770 stored on the computer readable medium 760 may include instructions to perform any of the methods described herein. For instance, in the illustrated embodiment, program instructions 770 include a controller module 772, calculation and decision module 774 and an alert module 776.

The controller module 772 can include instructions for operating the detection system 710, for example, the energy source 712 and the temperature sensor 714. For example, the controller module 772 may operate energy source 712 and the temperature sensor 714 during each of a set of pre-set measurement periods. In particular, the controller module 772 can include instructions for operating the energy source 712 to emit energy into a target region of an environment of interest (e.g., a portion of subsurface vasculature of a wearer of the device 700) and controlling the temperature sensor 714 to measure a temperature related to a flow rate of fluid in the environment being interrogated by the device 700.

The controller module 772 can also include instructions for operating a user interface 720. For example, controller module 772 may include instructions for displaying data collected by the detection system 710 and analyzed by the calculation and decision module 774, or for displaying one or more alerts generated by the alert module 776. Further, controller module 772 may include instructions to execute certain functions based on inputs accepted by the user interface 720, such as inputs accepted by one or more buttons disposed on the user interface.

Communication platform 730 may also be operated by instructions within the controller module 772, such as instructions for sending and/or receiving information via a wireless antenna, which may be disposed on or in the device 700. The communication interface 730 can optionally include one or more oscillators, mixers, frequency injectors, etc. to modulate and/or demodulate information on a carrier frequency to be transmitted and/or received by the antenna. In some examples, the device 700 is configured to indicate an output from the processor by modulating an impedance of the antenna in a manner that is perceivable by a remote server or other remote computing device.

Calculation and decision module 774 may include instructions for receiving data from and/or operating the data collection system 710, analyzing the data to determine a flow rate of fluid in the environment (e.g., a flow rate of blood in a portion of subsurface vasculature), analyzing the determined flow rate at one or more points in time to determine if a medical condition is indicated, determining a pressure of the fluid (e.g., a pressure of blood in a portion of subsurface vasculature) based on a determined flow rate, or other analytical processes relating to the environment proximate to the device 700. In particular, the calculation and decision module 774 may include instructions for determining, for each preset measurement time, a flow of fluid in the environment based on one or more temperature measurements made using the temperature sensor 714 and further based on operation of the energy source 712 to heat a portion of fluid in the environment of the device 700. The calculation and decision module 774 could include instructions to operate the energy source 712 to produce a variety of patterns of emitted energy, including one or more pulses of energy having respective properties (e.g., intensities, pulse widths, pulse waveforms), emitting a first energy having a first specified property (e.g., intensity) during a first period of time and a second energy having a second specified property during a second period of time, or according to some other application.

The program instructions of the calculation and decision module 774 may, in some examples, be stored in a computer-readable medium and executed by a processor located external to the device 700. For example, the device 700 could be configured to collect certain data regarding physiological parameters from the user and then transmit the data to a remote server, which may include a mobile device, a personal computer, the cloud, or any other remote system, for further processing.

The computer readable medium 760 may further contain other data or information, such as medical and health history of a user of the device 700, that may be useful in determining whether a medical condition is indicated. Further, the computer readable medium 760 may contain data corresponding to certain blood flow rate profile baselines, above or below which a medical condition is indicated. The baselines may be pre-stored on the computer readable medium 760, may be transmitted from a remote source, such as a remote server, or may be generated by the calculation and decision module 774 itself. The calculation and decision module 774 may include instructions for generating individual baselines for the user of the device 700 based on data collected over a certain number of measurement periods. For example, the calculation and decision module 774 may generate a baseline blood flow profile for each of a plurality of measurement periods by averaging a blood flow profile from one or more heart beat cycles during each of the measurement periods measured over the course of a few days, and store those baseline blood flow profiles in the computer readable medium 760 for later comparison. Baselines may also be generated by a remote server and transmitted to the device 700 via communication interface 730. The calculation and decision module 774 may also, upon determining that a medical condition is indicated, generate one or more recommendations for the user of the device 700 based, at least in part, on consultation of a clinical protocol. Such recommendations may alternatively be generated by the remote server and transmitted to the device 700.

In some examples, the collected physiological parameter data, baseline blood flow rate profiles, health state information input by device users and generated recommendations and clinical protocols may additionally be input to a cloud network and be made available for download by a user's physician. Trend and other analyses may also be performed on the collected data, such as physiological parameter data and health state information, in the cloud computing network and be made available for download by physicians or clinicians.

Further, physiological parameter and health state data from individuals or populations of device users may be used by physicians or clinicians in monitoring efficacy of a drug or other treatment. For example, high-density, real-time data may be collected from a population of device users who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by the calculation and decision module 774 that a medical condition is indicated, the alert module 776 may generate an alert via the user interface 720. The alert may include a visual component, such as textual or graphical information displayed on a display, an auditory component (e.g., an alarm sound), and/or tactile component (e.g., a vibration). The textual information may include one or more recommendations, such as a recommendation that the user of the device contact a medical professional, seek immediate medical attention, or administer a medication.

V. Illustrative Methods

Figure 8:
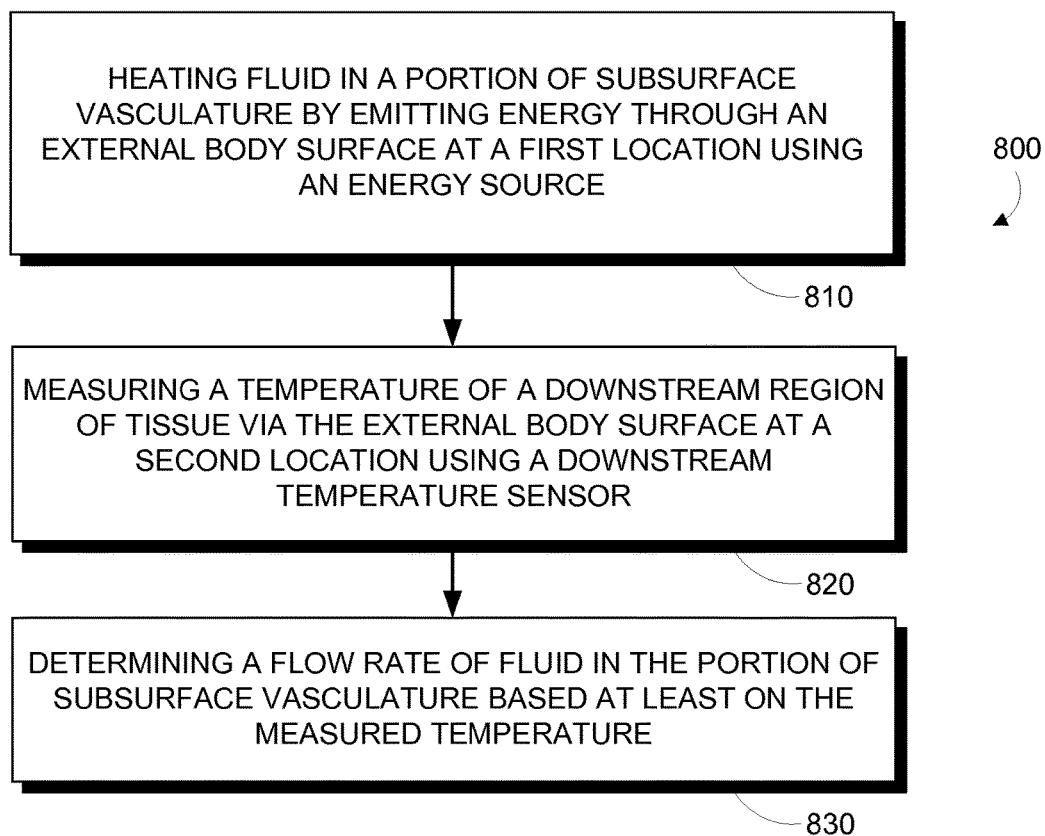
FIG. 8 is a flow chart of an example method.

FIG. 8 is a flowchart of a method 800 for measuring a flow rate of fluid (e.g., blood) in a portion of subsurface vasculature. The method 800 includes heating fluid in the portion of subsurface vasculature by emitting energy through an external body surface at a first location using an energy source 810. The emitted energy is such that a portion of fluid in the portion of subsurface vasculature absorbs a portion of the emitted energy and converts the absorbed energy into heat. The heated portion of fluid can subsequently be moved (i.e., by convection or other flow processes) downstream in the portion of subsurface vasculature at a rate corresponding to the flow rate of fluid in the portion of subsurface vasculature. Emitting energy can include emitting illumination having a specific wavelength or spectral profile, such that the illumination can be minimally absorbed by other elements in the environment of the portion of subsurface vasculature (e.g., skin, connective tissue, blood vessel walls). For example, the emitted beam of illumination could have a wavelength or wavelengths within a near-infrared (NIR) transparency window of biological tissue.

Emitting energy 810 can include emitting energy having a specified amplitude, intensity, wavelength, spectral profile, polarization, or other property. Further, emitting energy 810 can include emitting energy having different properties at different points in time. For example, it could include emitting a first energy having a first intensity during a first period of time and emitting a second energy having a second intensity during a second period of time. It could include emitting one or more pulses of energy having respective pulse widths, intensities, pulse waveforms (e.g., rectangular pulses, trapezoidal pulses, triangular pulses, raised cosine pulses) during respective periods of time. Such a plurality of pulses of emitted energy could be emitted at a specified frequency, e.g., a frequency between approximately 10 hertz and approximately 100 hertz. Other patterns or schemes of emitting energy and or operating the energy source are anticipated.

The method 800 additionally includes measuring a temperature of a downstream region of tissue via the external body surface at a second location using a downstream temperature sensor 820. The downstream region of tissue is a region of tissue downstream from the location at which the energy source heats fluid relative to the flow of fluid in the portion of subsurface vasculature. Measuring a temperature 820 could include making a direct measurement of temperature (e.g., using a temperature sensor that is in thermal contact with the downstream region of tissue via the external body surface at the second location) or an indirect measurement of temperature (e.g., by detecting an intensity, spectral profile, or other property of infrared light received from the downstream region of tissue through the external body surface at the second location). Measuring a temperature 820 could include making a single measurement at a specified point in time (e.g., relative to the timing of operation of the energy source) or at a plurality of specified points in time (e.g., at a plurality of points in time defined by a specified sample rate, e.g., 1 kilohertz). Measuring a temperature 820 could include measuring sufficient temperature information (e.g., measuring the temperature of the downstream region of tissue at a sufficient number of points in time) to determine a temperature waveform of the downstream region of tissue and/or a feature of the temperature waveform of the downstream portion of tissue (e.g., a timing, pulse width, rise time, fall time, or amplitude of a pulse of increased temperature, a rise time and/or timing of an increase in temperature).

The method 800 additionally includes determining a flow rate of fluid in the portion of subsurface vasculature based at least on the temperature measured by the downstream temperature sensor 830. This could include determining a difference between the measured temperature and a baseline temperature (e.g., a body temperature or other temperature of some other region of tissue as measured using a further temperature sensor). This could include determining a flow rate based on the properties and timing of operation of the energy source to emit energy. For example, the energy source could be operated to emit a first energy having first properties during a first period of time and a second energy having second properties during a second period of time, and the flow rate of fluid could be based on a temperature of a downstream region of tissue measured at a specified time, the properties of the first and second energies, and the timing of the first and second periods of time relative to the specified time of the temperature measurement. In some examples, determining a flow rate of fluid in the portion of subsurface vasculature 830 could include determining a feature of a temperature waveform of the downstream region of tissue based on one or more temperature measurements made using the downstream temperature sensor, and could further include determining a relative timing between the feature of the temperature waveform and a timing of operation of the energy source to heat fluid in the portion of subsurface vasculature. For example, a flow rate of fluid could be determined based on the result of the division of a specified distance between the first and second locations of the external body surface (e.g., a distance between approximately 1 millimeter and approximately 5 millimeters) by a determined difference in time between a change in the intensity of the energy emitted by the energy source (e.g., a changed from a first intensity to a second intensity) and a related feature of the temperature waveform of the downstream region of tissue (e.g., the timing of a rising edge of a pulse of increased temperature).

The method 800 could include additional steps or elements in addition to emitting energy 810, measuring a temperature 820, and determining a flow rate of fluid in the portion of subsurface vasculature 830. For example, the energy source and the downstream temperature sensor could be disposed in a wearable device, and the method 800 could include mounting the wearable device to an external body surface of the wearer proximate to the portion of subsurface vasculature. The method could include indicating a determined flow rate of fluid to a user using a user interface of the device or to some other person or system(s) by some other means (e.g., a wireless communications component of the wearable device).

The method 800 could include determining some other information about a wearer based on one or more determined flow rates of fluid in the portion of subsurface vasculature during one or more periods of time. For example, a determined flow rate of blood in the portion of subsurface vasculature determined at one or more points in time could be used to determine a blood pressure in the portion of subsurface vasculature. One or more determined flow properties in the portion of subsurface vasculature could be used to determine a health state of the wearer. For example, a plurality of flow rates of blood determined at a respective plurality of points in time could be used to determine a heart rate of the user that could further be used to determine a health state of the wearer (e.g., tachycardia, bradycardia, sleep apnea, irregular heartbeat). Additionally or alternatively, a plurality of flow rates of blood could be used to determine a flow and/or pressure profile of the blood that could further be used to determine a health state of the wearer (e.g., hypertension, aortic regurgitation). Other additional steps of the method 800 are anticipated.

Calibration data could be used to determine a pressure of blood in the portion of subsurface vasculature based on a determined flow rate of blood in the portion of subsurface vasculature. Calibration data could include information about models, functions, lookup tables, or other algorithms used to determine a blood pressure based on a determined blood flow rate. Such data could be manually determined and/or input into a device that is implementing the method 800. Additionally or alternatively, the calibration data could be determined through a calibration method whereby one or more detected values of blood flow rate could be associated with corresponding one or more values of blood pressure. The values of blood pressure could be measured using a sphygmomanometer or other apparatus configured to directly measure blood pressure in the portion of subsurface vasculature. In some examples, calibration data could be generated by detecting one or more blood flow rates when the portion of subsurface vasculature is elevated to two or more different elevations relative to the heart of the body containing the portion of subsurface vasculature (e.g., by raising and/or lowering an arm containing the portion of subsurface vasculature).

Figure 9:
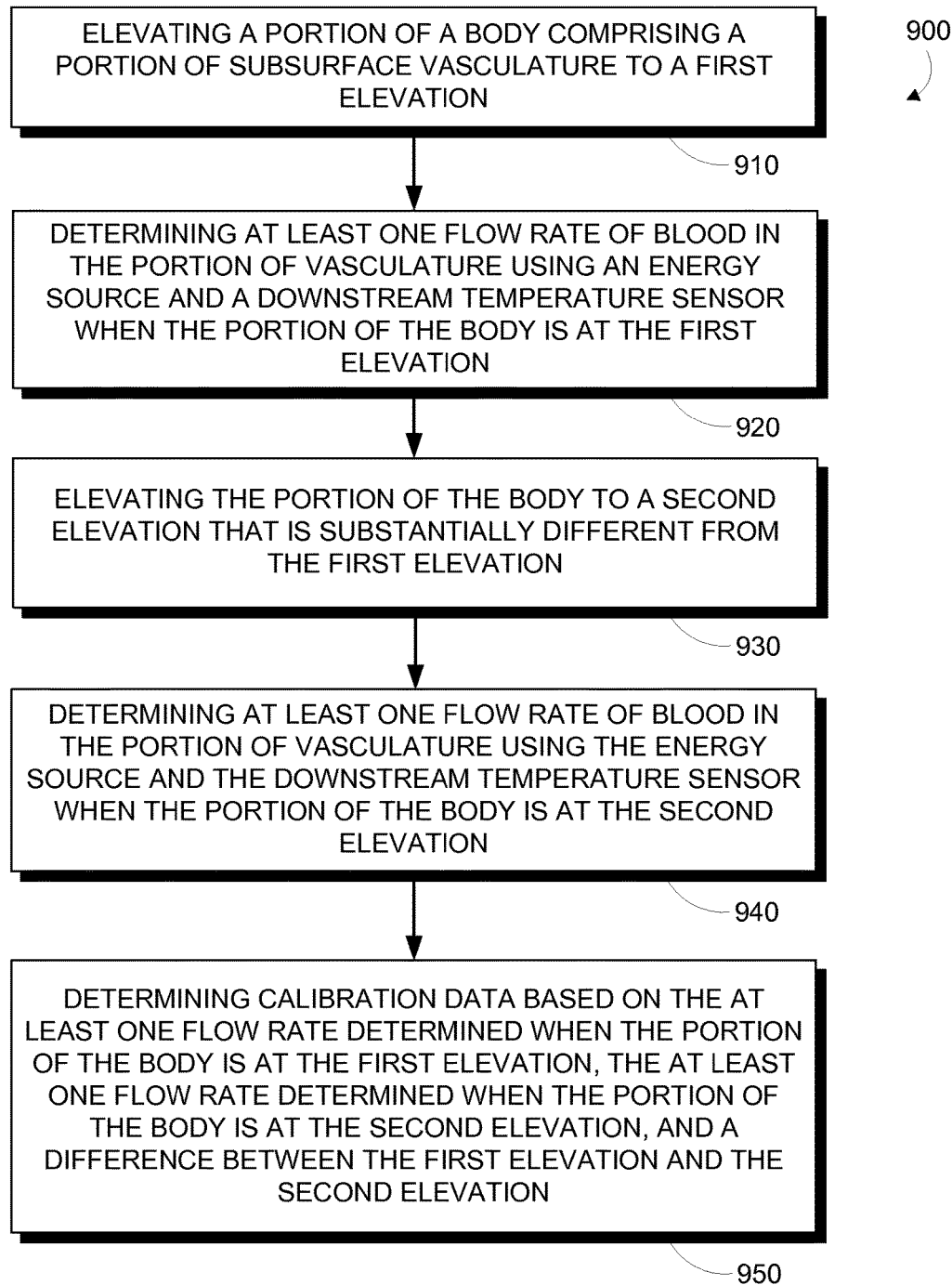
FIG. 9 is a flow chart of an example method.

FIG. 9 is a flowchart of a method 900 for calibration data that could be used to determine a pressure of blood in a portion of subsurface vasculature based on at least one measured and/or detected flow rate of blood in the portion of subsurface vasculature. The method 900 includes elevating a portion of a body comprising the portion of subsurface vasculature to a first elevation 910. This could include elevating the portion of the body by actions of the body (e.g., activation of muscles of the body to elevate the portion of subsurface vasculature, by raising and/or lowering an arm). This could include elevating the portion of subsurface vasculature to a specified elevation (e.g., according to instructions or some sort of elevation feedback signal). The elevation could be an elevation relative to the heart of the body containing the portion of subsurface vasculature. Additionally or alternatively, the first elevation could be arbitrary and/or chosen by a user, and the value of the first elevation could be detected and/or input into a system performing the method 900 by the user.

The method 900 includes determining at least one flow rate of blood in the portion of subsurface vasculature using an energy source and a downstream temperature sensor when the portion of the body is at the first elevation 920. This step could be performed as described elsewhere herein, i.e., by operation of the energy source to heat a portion of blood in the portion of subsurface vasculature, measurement of at least one temperature by the downstream temperature sensor, and making a determination of a flow rate of blood in the portion of subsurface vasculature. The energy source and temperature sensor could be included in a wearable device or other apparatus as described herein.

The method 900 includes elevating the portion of a body comprising the portion of subsurface vasculature to a second elevation that is substantially different from the first elevation 930. This could include elevating the portion of the body by actions of the body (e.g., activation of muscles of the body to elevate the portion of subsurface vasculature, raising and/or lowering an arm). This could include elevating the portion of subsurface vasculature to a specified elevation (e.g., according to instructions or some sort of elevation feedback signal). The elevation could be an elevation relative to the heart of the body containing the portion of subsurface vasculature. Additionally or alternatively, the second elevation could be arbitrary and/or chosen by a user, and the value of the second elevation could be detected and/or input into a system performing the method 900 by the user.

The method 900 includes determining at least one flow rate of blood in the portion of subsurface vasculature using the energy source and the downstream temperature sensor when the portion of the body is at the second elevation 940. This step could be performed as described elsewhere herein, i.e., by operation of the energy source to heat a portion of blood in the portion of subsurface vasculature, measurement of at least one temperature by the downstream temperature sensor, and making a determination of a flow rate of blood in the portion of subsurface vasculature. The energy source and temperature sensor could be included in a wearable device or other apparatus as described herein.

The method 900 includes determining calibration data based on the at least one blood flow rate determined when the portion of the body is at the first elevation, the at least one blood flow rate determined when the portion of the body is at the second elevation, and a difference between the first elevation and the second elevation 950. The calibration data could take a variety of forms related to the method used to determine a blood pressure based on a determined blood flow rate and the calibration data could be determined from the listed information accordingly. For example, the respective at least one blood flow rates determined at the first and second elevations could be maximum blood flow rates corresponding to points in respective heartbeats corresponding to a systolic blood pressure in the portion of subsurface vasculature. The difference between a systolic blood pressure when the portion of subsurface vasculature is at the first elevation and a systolic blood pressure when the portion of subsurface vasculature is at the second elevation could be related to a difference in pressure corresponding to a difference in elevation in a water column (or column of other fluid having a density similar to the wearer's blood) substantially equal to the difference between the first and second elevations. The first and second elevations could be elevations relative to the heart of the body containing the portion of subsurface vasculature. Thus, a difference in the maximum blood flow rates corresponding to the difference in pressure determined using the difference between the first and second elevations could be used to determine the calibration data.

The method 900 could include additional steps or elements in addition to those described above (910, 920, 930, 940, 950). For example, the portion of the body could be elevated to additional elevations at which additional corresponding blood flow rates could be determine/detected, and the calibration data could be determined based on the additional elevations and additional determined/detected blood flow rates. The method 900 could be performed a first time, and the determined calibration data could be used to determine blood pressures during a first period of time. The method could be performed subsequently to replace, update, and/or refine the calibration data determined during previous performances of the method 900. The method could include indicating determined calibration, pressure, and/or flow rate data to a user using a user interface of the device or to some other person or system(s) by some other means (e.g., a wireless communications component of the wearable device). Other additional and/or alternative steps of the method 900 are anticipated.

CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Moreover, it is particularly noted that while devices, systems, methods, and other embodiments are described herein by way of example as being employed to detect blood flow in portions of subsurface vasculature of a human body, it is noted that the disclosed devices, systems, and methods can be applied in other contexts as well. For example, detection systems configured to detect fluid flow rates using energy sources and temperature sensors as disclosed herein may be included in wearable (e.g., body-mountable) and/or implantable devices. In some contexts, such a detection system is situated to be substantially encapsulated by biocompatible polymeric material suitable for being in contact with bodily fluids and/or for being implanted. In one example, an implantable medical device that includes such a detection system may be encapsulated in biocompatible material and implanted within a host organism. Such body-mounted and/or implanted detection systems can include circuitry configured to operate energy sources, temperature sensors, or other elements to enable detection of fluid flow rates by detecting changes over time in a detected temperature of fluids relative to heating of the fluid by the energy source. The detection system can also include a communication system for wirelessly indicating detected and/or determined fluid flows.

In other examples, devices, systems, and methods disclosed herein may be applied to measure flow rates of fluids that are not in or on a human body. For example, detection systems disclosed herein may be included in body-mountable and/or implantable devices used to measure flow rates of a fluid of an animal. In another example, devices, systems, and methods disclosed herein may be applied to measure flow rates of an environmental fluid, such as a fluid in a river, lake, marsh, reservoir, water supply, sanitary sewer system, storm sewer system, or the atmosphere. In another example, devices, systems, and methods disclosed herein may be applied to measure flow rates of a fluid that is part of a process, such as a waste treatment process, industrial process, pharmaceutical synthesis process, food preparation process, fermentation process, or medical treatment process Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A device comprising:
   an energy source;
   a downstream temperature sensor; and
   a controller, wherein the controller comprises a computing device programmed to perform operations comprising:
   operating the energy source to emit first energy having a first intensity during a first period of time, wherein the first energy is emitted through an external body surface at a first location into a portion of subsurface vasculature such that fluid in the portion of subsurface vasculature is heated;
   operating the energy source to emit second energy having a second intensity during a second period of time, wherein the second energy is emitted through the external body surface at the first location into the portion of subsurface vasculature such that fluid in the portion of subsurface vasculature is heated, and wherein the second intensity differs from the first intensity;
   operating the downstream temperature sensor to measure the temperature over time of a downstream region of tissue via the external body surface at a second location at a plurality of points in time subsequent to the beginning of the first period of time, wherein the downstream region of tissue is downstream from the first location with respect to fluid flow in the portion of subsurface vasculature; and
   determining a speed of fluid in the portion of subsurface vasculature based on the temperatures measured by the downstream temperature sensor, wherein said determining the speed of fluid in the portion of subsurface vasculature based on the temperatures measured by the downstream temperature sensor comprises (i) identifying a feature within the temperature measurements of the downstream region of tissue measured at the plurality of points in time and (ii) determining a time difference between the first period of time and a timing of the identified feature.

2. The device of claim 1, further comprising a mount configured to mount the energy source and the downstream temperature sensor to the external body surface.

3. The device of claim 2, wherein the external body surface is a wrist location.

4. The device of claim 2, wherein the energy source is a light source, and wherein emitting energy through an external body surface at a first location into a portion of subsurface vasculature comprises emitting a beam of illumination through the external body surface into the portion of subsurface vasculature.

5. The device of claim 4, wherein the light source is a laser.

6. The device of claim 1, wherein the second location is separated from the first location by a specified distance, wherein the specified distance is between approximately 1 millimeter and approximately 5 millimeters.

7. The device of claim 1, further comprising a plurality of further temperature sensors that are operable to measure temperatures of respective regions of tissue via respective locations of the external body surface, wherein the downstream temperature sensor and further temperature sensors are arranged in a linear array, and wherein the operations further comprise operating the plurality of further temperature sensors, and wherein determining a speed of fluid in the portion of subsurface vasculature is further based on temperatures measured by the plurality of further temperature sensors.

8. The device of claim 1, wherein the downstream temperature sensor detects infrared light received from the downstream region of tissue via the second location of the external body surface.

9. The device of claim 8, wherein the downstream temperature sensor comprises an infrared camera, wherein the infrared camera is operable to image the portion of subsurface vasculature by detecting near infrared light.

10. A method comprising:
    heating fluid in a portion of subsurface vasculature during a first period of time, wherein heating fluid in the portion of subsurface vasculature during the first period of time comprises emitting first energy having a first intensity through an external body surface at a first location into the portion of subsurface vasculature using an energy source;
    heating fluid in the portion of subsurface vasculature during a second period of time, wherein heating fluid in the portion of subsurface vasculature during the second period of time comprises emitting second energy having a second intensity through the external body surface at the first location into the portion of subsurface vasculature using the energy source, and wherein the second intensity differs from the first intensity;
    measuring a temperature over time of a downstream region of tissue via the external body surface at a second location at a plurality of points in time subsequent to the beginning of the first period of time, wherein the downstream region of tissue is downstream from the first location with respect to fluid flow in the portion of subsurface vasculature; and
    determining a speed of fluid in the portion of subsurface vasculature based on the temperatures measured by the downstream temperature sensor, wherein said determining the speed of fluid in the portion of subsurface vasculature based on the temperatures measured by the downstream temperature sensor comprises (i) identifying a feature within the temperature measurements of the downstream region of tissue measured at the plurality of points in time and (ii) determining a time difference between the first period of time and a timing of the identified feature.

11. The method of claim 10, further comprising:
    imaging the portion of subsurface vasculature using an infrared camera, wherein the infrared camera is operable to image the portion of subsurface vasculature by detecting near infrared light.

12. The method of claim 10, wherein the energy source and the downstream temperature sensor are disposed in a wearable device, wherein the wearable device further comprises a mount, and further comprising:
    mounting the wearable device to the external body surface using the mount.

13. The method of claim 10, further comprising emitting, using the energy source, a plurality of pulses of energy during a plurality of respective periods of time.

14. The method of claim 13, wherein the plurality of respective periods of time are regularly spaced in time, wherein the regular spacing of the respective periods of time represent a frequency of the pulses of energy, wherein the frequency of the pulses of energy is a specified frequency, wherein the specified frequency is between approximately 10 hertz and approximately 100 hertz.

15. The method of claim 10, wherein the fluid is blood, further comprising:
   determining a pressure of blood in the portion of subsurface vasculature, wherein determining a pressure of blood in the portion of subsurface vasculature comprises determining a pressure based on at least one determined speed of blood in the portion of subsurface vasculature.

16. The method of claim 15, wherein determining a pressure based on at least one determined speed of blood in the portion of subsurface vasculature comprises using calibration data to determine a pressure based on the at least one determined speed of blood, wherein calibration data are determined by a calibration process, wherein the calibration process comprises:
   elevating a portion of the body comprising the portion of subsurface vasculature to a first elevation;
   determining at least one speed of blood in the portion of subsurface vasculature using the energy source and the downstream temperature sensor when the portion of the body is at the first elevation;
   elevating the portion of the body comprising the portion of subsurface vasculature to a second elevation, wherein the second elevation is substantially different from the first elevation;
   determining at least one speed of blood in the portion of subsurface vasculature using the energy source and the downstream temperature sensor when the portion of the body is at the second elevation; and
   determining calibration data, wherein determining calibration data comprises generating the calibration data based at least on the at least one speed of blood determined when the portion of the body is at the first elevation, the at least one speed of blood determined when the portion of the body is at the second elevation, and a difference between the first elevation and the second elevation.

17. A device comprising:
   an energy source;
   a downstream temperature sensor; and
   an upstream temperature sensor,
   a controller, wherein the controller comprises a computing device programmed to perform operations comprising:
   operating the energy source to emit first energy having a first intensity during a first period of time, wherein the first energy is emitted through an external body surface at a first location into a portion of subsurface vasculature such that fluid in the portion of subsurface vasculature is heated;
   operating the energy source to emit second energy having a second intensity during a second period of time, wherein the second energy is emitted through the external body surface at the first location into the portion of subsurface vasculature such that fluid in the portion of subsurface vasculature is heated, and wherein the second intensity differs from the first intensity;
   operating the downstream temperature sensor to measure the temperature over time of a downstream region of tissue via the external body surface at a second location at a plurality of points in time subsequent to the beginning of the first period of time wherein the downstream region of tissue is downstream from the first location with respect to fluid flow in the portion of subsurface vasculature; and
   operating the upstream temperature sensor to measure the temperature over time of an upstream region of tissue via the external body surface at a third location at the plurality of points in time subsequent to the beginning of the first period of time, wherein the upstream region of tissue is upstream from the first location with respect to fluid flow in the portion of subsurface vasculature,
   determining a speed of fluid in the portion of subsurface vasculature based on the temperatures measured by the downstream temperature sensor and the upstream temperature sensor, wherein said determining the speed of fluid in the portion of subsurface vasculature based on the temperatures measured by the downstream temperature sensor and the upstream temperature sensor comprises:
   (i) determining a temperature difference signal between the temperature over time of the downstream region of tissue and the temperature over time of the upstream region of tissue,
   (ii) identifying a feature within the temperature difference signal measured for the plurality of points in time and
   (iii) determining a time difference between the first period of time and a timing of the identified feature.

18. A device comprising:
   an energy source;
   a downstream temperature sensor; and
   a further temperature sensor,
   a controller, wherein the controller comprises a computing device programmed to perform operations comprising:
   operating the energy source to emit first energy having a first intensity during a first period of time, wherein the first energy is emitted through an external body surface at a first location into a portion of subsurface vasculature such that fluid in the portion of subsurface vasculature is heated;
   operating the energy source to emit second energy having a second intensity during a second period of time, wherein the second energy is emitted through the external body surface at the first location into the portion of subsurface vasculature such that fluid in the portion of subsurface vasculature is heated, and wherein the second intensity differs from the first intensity;
   operating the downstream temperature sensor to measure the temperature over time of a downstream region of tissue via the external body surface at a second location at a plurality of points in time subsequent to the beginning of the first period of time wherein the downstream region of tissue is downstream from the first location with respect to fluid flow in the portion of subsurface vasculature; and
   operating the further temperature sensor to measure the temperature over time of a further region of tissue via the external body surface at a third location at the plurality of points in time subsequent to the beginning of the first period of time, wherein the further region of tissue is a different region of tissue than the downstream region of tissue,
   determining a speed of fluid in the portion of subsurface vasculature based on the temperatures measured by the downstream temperature sensor and the further temperature sensor, wherein said determining the speed of fluid in the portion of subsurface vasculature based on the temperatures measured by the downstream temperature sensor and the further temperature sensor comprises:
(i) determining a temperature difference signal between the temperature over time of the downstream region of tissue and the temperature over time of the further region of tissue,
(ii) identifying a feature within the temperature difference signal measured for the plurality of points in time and
(iii) determining a time difference between the first period of time and a timing of the identified feature.

* * * * *